(12) United States Patent
Carrillo, Jr. et al.

(10) Patent No.: US 11,737,762 B2
(45) Date of Patent: Aug. 29, 2023

(54) CLIP DEVICES, SYSTEMS, AND METHODS FOR ENGAGING TISSUE

(71) Applicant: Boston Scientific Scimed, Inc., Maple Grove, MN (US)

(72) Inventors: Oscar R. Carrillo, Jr., Middletown, CT (US); Katie Olmeda, Maynard, MA (US); Routha Sim, Lowell, MA (US); Todd M. Pfizenmaier, Worcester, MA (US); James J. Scutti, Norwell, MA (US); Barry Weitzner, Acton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 287 days.

(21) Appl. No.: 16/668,341

(22) Filed: Oct. 30, 2019

(65) Prior Publication Data
US 2020/0129181 A1 Apr. 30, 2020

Related U.S. Application Data

(60) Provisional application No. 62/837,041, filed on Apr. 22, 2019, provisional application No. 62/753,540, filed on Oct. 31, 2018.

(51) Int. Cl.
*A61B 17/122* (2006.01)
*A61B 17/00* (2006.01)

(52) U.S. Cl.
CPC ............. *A61B 17/1227* (2013.01); *A61B 2017/00269* (2013.01); *A61B 2017/00296* (2013.01)

(58) Field of Classification Search
CPC .............. A61B 17/1227; A61B 17/128; A61B 17/1285; A61B 17/122; A61B 17/08;
(Continued)

(56) References Cited

U.S. PATENT DOCUMENTS

| 8,038,612 B2 | 10/2011 | Paz |
| 8,172,859 B2 | 5/2012 | Matsuno et al. |

(Continued)

FOREIGN PATENT DOCUMENTS

| EP | 3278703 A1 | 2/2018 |
| WO | 9713466 A1 | 4/1997 |
| WO | 2013041960 A1 | 3/2013 |

OTHER PUBLICATIONS

Invitation to Pay Additional Fees and, Where Applicable, Protest Fee, for the International Patent Application No. PCT/US2019/058732, mailed Feb. 3, 2020, 12 pages.

(Continued)

*Primary Examiner* — Brooke Labranche
(74) *Attorney, Agent, or Firm* — Seager, Tufte & Wickhem, LLP

(57) ABSTRACT

The present disclosure relates to compression clips, and more specifically, to compression clips delivered to a target site through an endoscope for use in tissue resection, for example, within the gastrointestinal tract. In examples, clips are configured to be actuatable in response to a compressive force to transition between an open configuration and a closed configuration. In an embodiment, a tissue clipping device may include a first member with a plurality of arms. Each of the arms may extend from a first end to a second end, and the first end of each arm may be received within the first member. The arms may be movable between the open configuration and the closed configuration. A second member may be slidably disposed with respect to the first member.

20 Claims, 13 Drawing Sheets

(58) Field of Classification Search
CPC ........... A61B 2017/00269; A61B 2017/00296; A61B 2017/0488
See application file for complete search history.

(56) References Cited

U.S. PATENT DOCUMENTS

| | | | |
|---|---|---|---|
| 8,397,335 | B2 | 3/2013 | Gordin et al. |
| 8,945,155 | B2 | 2/2015 | Gordin et al. |
| 8,974,371 | B2 | 3/2015 | Durgin et al. |
| 9,289,216 | B2 | 3/2016 | Weisshaupt et al. |
| 9,445,812 | B2 | 9/2016 | Dlson et al. |
| 9,463,003 | B2 | 10/2016 | Gordin et al. |
| 10,143,459 | B2 | 12/2018 | Heftman |
| 2002/0177861 | A1* | 11/2002 | Sugiyama ............ A61B 17/122 606/151 |
| 2005/0143767 | A1* | 6/2005 | Kimura ................. A61B 50/30 606/158 |
| 2007/0135678 | A1 | 6/2007 | Suzuki |
| 2008/0004637 | A1 | 1/2008 | Klassen et al. |
| 2013/0253275 | A1 | 9/2013 | Ransden et al. |

OTHER PUBLICATIONS

Sakamoto, N., et al., "Endoscopic submucosal dissection of large colorectal tumors by using a novel spring-action S-O clip for traction (with video)", Gastrointestinal Endoscopy 69(7):1370-1374 (2009).

Fujii, T., et al., "A novel endoscopic suturing technique using a specially designed so-called "8-ring" in combination with resolution clips (with videos)", Gastrointestinal Endoscopy 66(6):1215-1220 (2007).

Matsumoto, K., et al., "T1594: A New Traction Device for Gastric Endoscopic Submucosal Dissecton (ESD): Two-Point Fixed by Latex Traction for Early Gastric Cancer", Gastrointestinal Endoscopy, 71(5):AB317 (2010).

Imaeda, H., et al., "Advanced endoscopic submucosal dissection with traction", World Journal of Gastrointestinal Endoscopy 6(7):286-295 (2014).

Sakamoto, N., et al.,"'Loop Clip' a new closure device for large mucosal defects after EMR and ESD", Endoscopy 40: E97-E98 (2008).

Fujihara, S., et al., "Management of a large mucosal defect after duodenal endoscopic resection", World Journal of Gastroenterology, 22(29):6595-6609 (2016).

Miori, H., et al., "The Loop Clip is Useful for Closing Large Mucosal Defects After Colorectal Endoscopic Submucosal Dissection: A Preliminary Clinical Study", Digestive Endoscopy 23:330-331 (2011).

Tsuji, K., et al., "Recent traction methods for endoscopic submucosal dissection", World Journal of Gastroenterology, 22(26):5917-5926 (2016).

Ritsuno, H., et al., "Prospective clinical trial of traction device-assisted endoscopic submucosal dissection of large superficial colorectal tumors using the S-O clip", Surgical Endoscopy 28:3143-3149 (2014).

Sakamoto, N., et al., "The facilitation of a new traction device (S-O clip) assisting endoscopic submucosal dissection tor superficial colorectal neoplasms", Endoscopy, 40:E94-E95 (2008).

Takeda, T., et al., "Traction device to remove an adenoma in the appendiceal orifice by endoscopic submucosal dissection", Endoscopy 45:E239-E240 (2013).

Kato, M., et al., "Technical feasibility of line-assisted complete closure technique for large mucosal defects after colorectal endoscopic submucosal dissection", Endoscopy International Open, 5(1):E11-E16 (2017) DOI: http://dx.doi.org/10.1055/s-0042-121002.

* cited by examiner

CLIP DEVICES, SYSTEMS, AND METHODS FOR ENGAGING TISSUE

PRIORITY

This application claims the benefit of priority under 35 USC § 119 to U.S. Provisional Patent Application Ser. No. 62/753,540, filed Oct. 31, 2018 and titled, "Universal Clip Enabling Opening from Any Angle," and to U.S. Provisional Patent Application Ser. No. 62/837,041, filed Apr. 22, 2019 and titled, "Clip Devices, Systems, and Methods For Engaging Tissue" both of which are incorporated by reference herein in their entirety and for all purposes.

FIELD

The present disclosure relates to clips, and more specifically, to compression clips delivered to a target site through an endoscope for use in tissue resection, for example, within the gastrointestinal tract.

BACKGROUND

Manipulating devices for engaging tissue may require involved techniques for positioning and orienting the devices and associated medical instruments. For example, endoscopic submucosal dissection (ESD) is a procedure that enables tissue resection within the gastrointestinal tract. One aspect of ESD that may be difficult is the positioning and maneuvering (e.g., retraction) of the resected tissue flap during and after cutting.

It is with these considerations in mind that a variety of advantageous medical outcomes may be realized by the medical devices, systems, and methods of the present disclosure.

SUMMARY

In various embodiments, the present disclosure relates to a tissue clipping device that may include an opening mechanism configured to be grasped from a plurality of angles relative to a longitudinal axis of the clip device. The opening mechanism may include first and second members configured to be displaced relative to one another along the longitudinal axis of the clip device into an opening configuration in response to an application of a compressive force. The opening mechanism may include a cam member extending from a first end to a second end, the first end may be fixedly coupled to the first member and may be slidably coupled to the second member. A plurality of clip arms may each extend from a first end to a second end, and the first end of each clip arm may be received within the opening mechanism. The clip arms may be movable between an open configuration, in which second ends of the clip arms are separated from one another, and a closed tissue clipping configuration, in which second ends of the clip arms are moved toward one another. Each of the clip arms may include a spring portion configured to form a spring space between the spring portions. The cam member may move into the spring space when the first and second members are moved to the opening configuration so that, as the cam member is moved into the spring space, the cam member may deflect the spring members away from one another to move the clip arms to the open configuration.

In the described and other embodiments, the first and second members may include angled surfaces configured to move the first and second members in opposite directions away from each other in response to an application of a compressive force to the angled surfaces. The cam member may include a U-bend at the second end and two legs extending from the U-bend to the first end. The legs may be configured to be slidably received through the second member and may be immovably coupled to the first member. The cam member may include a wedge centrally positioned on the U-bend. The wedge may extend from the U-bend toward the first end between the legs of the cam member. The wedge may be configured to be received in the space between the spring portions such that movement of the wedge toward the second member may cause the wedge to deflect the spring portions away from one another to move the clip arms to the open configuration. The wedge may taper from a first end at the first end of the cam member to a second end between the legs of the cam member. The clip arms may be formed of a single wire bent at a medial portion, the medial portion may form the first ends of the clip arms. The second member of the opening mechanism may include a channel configured to receive the first ends of the clip arms. The clip arms may be biased to the closed configuration.

In various embodiments, the present disclosure also relates to a clip device comprising an opening mechanism that may include a gripping member. A deformable fluid chamber may be configured to be grasped from a plurality of angles. The fluid chamber may define a cavity therein that may be configured to be filled with a fluid. A balloon chamber may define a cavity therein. The balloon chamber may be inflatable from a resting state when filled with the fluid. At least one connection channel may extend from a first end open to the cavity of the fluid chamber to a second end open to the cavity of the balloon chamber to provide fluid communication between the fluid chamber and the balloon chamber such that, as the fluid chamber is compressed, fluid may be dispelled from the fluid chamber to the balloon chamber via the connection channel to inflate the balloon chamber. The clip device may also include clip arms extending from a first end to a second end. The first end may be coupled to the gripping member. The clip arms may be movable between an open configuration, in which second ends of the clip arms may be separated from one another, and a closed tissue clipping configuration, in which second ends of the clip arms may be moved toward one another. Each of the clip arms may include a spring portion configured to form a spring space between the spring portions. The spring space may receive the balloon chamber such that, when the balloon chamber inflates, the spring members may be deflected away from one another to move the clip arms to the open configuration.

In the described and other embodiments, the gripping member may include an extension extending through a central closed lumen in the fluid chamber to couple to the first ends of the clip arms. The fluid chamber may be filled with one of saline, water, gel, or other suitable fluid. The spring portions may be formed as bends in the clip arms, a bend may extend toward a central axis of the clip device. The clip arms may be biased to the closed configuration. The gripping member may be configured to be gripped by a gripper tool. The clip arms may be formed of a wire bent at a medial portion to form the first end of the clip arms.

In various embodiments, the present disclosure also relates to a method of positioning a clip system on a target tissue from a plurality of angles. A clip system may be inserted to a target site via a working channel of an insertion device. The clip system may include a first clip device. The first clip device may include an opening mechanism that may be configured to be grasped from a plurality of angles relative to a longitudinal axis of the clip device. The opening mechanism may include a first and a second member that may be configured to be displaced relative to one another along the longitudinal axis of the clip device into an opening configuration in response to an application of a compressive force. The opening mechanism may include a cam member extending from a first end to a second end, and the first end may be fixedly coupled to the first member and slidably coupled to the second member. A plurality of clip arms may each extend from a first end to a second end, and the first end of each clip arm may be received within the opening mechanism. The clip arms may be movable between an open configuration, in which second ends of the clip arms may be separated from one another, and a closed tissue clipping configuration, in which second ends of the clip arms may be moved toward one another. Each of the clip arms may include a spring portion configured to form a spring space between the spring portions. The cam member may move into the spring space when the first and second members are moved to the opening configuration so that, as the cam member is moved into the spring space, the cam member may deflect the spring members away from one another to move the clip arms to the open configuration. The method may include inserting a gripper tool to the target site via the working channel. The method may include grasping the opening mechanism of the first clip device via the gripper tool to move the clip arms of the first clip device to the open configuration. The method may include positioning the clip arms of the first clip device so that a first portion of target tissue is received between the clip arms of the first clip device. The method may include releasing the gripper tool to move the clip arms of the first clip device from the open configuration to the closed configuration to clip the first portion of target tissue.

In the described and other embodiments, the method may further include coupling the first clip device to a second clip device via a tether. In the described and other embodiments, a method may further include grasping an opening mechanism of the second clip device from the gripper tool to move clip arms of the second clip device to an open configuration. The method may include positioning a second portion of target tissue between the clip arms of the second clip device. The method may include releasing the gripper tool to move the clip arms of the second clip device from the open configuration to the closed tissue clipping configuration to clip the second portion of target tissue, the location of the second target portion of tissue may be selected so that, when the first and second target portions of tissue are clipped by the first and second clip devices, respectively, a desired level of tension may be applied to the first target portion of tissue via the tether. The first and second members may include angled surfaces configured to move the first and second members in opposite directions away from the applied compressive force. The clip arms may be biased to the closed configuration.

In various embodiments, the present disclosure relates to a tissue clipping device that may include a first member. One or more arms, each extending from a first end to a second end, may each be received within the first member. Each of the arms may include a spring portion configured to form a spring space between the spring portions. The arms may be movable between an open configuration, in which the spring portions of the arms are biased toward one another, and a closed configuration, in which the spring portions of the arms are separated apart from one another. A second member may be slidably disposed about the plurality of arms. A grasper may have a first end engaged between the arms and a second end that may include jaws configured to engage tissue. The first member and the second member may be configured to be grasped from a plurality of angles relative to a longitudinal axis of the clipping device, and may be configured to be displaced relative to one another along the longitudinal axis of the clipping device in response to an application of a compressive force. A cam member may extend from a first end to a second end, the first end may be fixedly coupled to the second member and the second end may be configured to engage the spring space. The second end of the cam member may be moveable into and out of engagement with the spring space when the first and second members are displaced relative to one another, such that when the first and second members are displaced apart from one another the second end of the cam member may move out of engagement with the spring space and the arms may assume the open configuration, and when the first and second members are displaced toward one another the second end of the cam member may move into engagement with the spring space and the arms transition to the closed configuration.

In the described and other embodiments, the first and second members may include angled surfaces configured to displace the first and second members apart from one another in response to an application of a compressive force to the angled surfaces. The cam member may include a U-bend at the second end of the cam member and two legs may extend from the U-bend to the first end of the cam member. The cam member may include a wedge centrally positioned on the U-bend, and the wedge may taper to a smaller width transverse to the longitudinal axis as the wedge extends from the U-bend between the legs toward the first end of the cam member. The wedge may be configured to engage the spring space. The arms may be formed of a single wire bent at a medial portion, and the medial portion may form the first ends of the arms. The first member may include a channel configured to fixedly receive the first ends of the arms. The arms may be biased to the open configuration. The grasper may include first and second grasper arms in a crossing configuration. The second ends may move away from each other when the first ends move closer together.

In various embodiments, the present disclosure also relates to a tissue clipping device that may include a first member. The device may include a plurality of arms. Each of the arms may extend from a first end to a second end. The first end of each arm may be received within the first member. The arms may be movable between an open configuration and a closed configuration. A second member may be slidably disposed with respect to the first member. The first member and the second member may be configured to be grasped from a plurality of angles relative to a longitudinal axis of the clipping device. The first member and the second member may be configured to be displaced relative to one another along the longitudinal axis of the clipping device in response to an application of a compressive force. The first and second members may include angled surfaces configured to displace the first and second members apart from one another in response to an application of a compressive force to the angled surfaces such that when the first and second members are displaced with respect to each other the arms may transition between the open configuration and the closed configuration.

In various embodiments, the present disclosure relates to a tissue clipping device that may include a first member. One or more arms, each extending from a first end to a second end, may be received within the first member. The arms may be movable between an open configuration, in which the second ends of the arms may be separated apart from one another, and a closed configuration, in which the second ends of the arms may be biased toward one another. Each of the arms may include a spring portion configured to form a spring space between the spring portions. A second member may be slidably disposed about the plurality of arms. The second member may have one or more channels internal to the second member that may be engageable with opposing sloped surfaces of the arms. The first member and the second member may be configured to be grasped from a plurality of angles relative to a longitudinal axis of the clipping device, and may be configured to be displaced relative to one another along the longitudinal axis of the clipping device in response to an application of a compressive force. The one or more channels may be moveable into and out of engagement with the opposing sloped surfaces of the arms when the first and second members are displaced relative to one another to transition the arms between the closed configuration and open configuration.

In the described and other embodiments, the opposing sloped surfaces of the arms may slope toward each other and the longitudinal axis, such that when the first and second members are displaced apart from one another the one or more channels may be moved into engagement with the sloped surfaces separating the arms apart into the open configuration, and when the first and second members are displaced toward one another the one or more channels may be moved out of engagement with the sloped surfaces and the arms transition to the closed configuration. In other embodiments, the opposing sloped surfaces of the arms may slope away from each other and the longitudinal axis, such that when the first and second members are displaced apart from one another the one or more channels may be moved into engagement with the sloped surfaces space bringing the arms together into the open configuration, and when the first and second members are displaced toward one another the one or more channels may be moved out of engagement with the sloped surfaces and the arms transition to the closed configuration.

In the described and other embodiments, the arms may be biased to the closed configuration with the arms toward each other in the spring space. The first and second members may include angled surfaces configured to displace the first and second members apart from one another in response to an application of a compressive force to the angled surfaces. The arms may be formed of a single body bent at a medial portion. The medial portion may form the first ends of the arms. A grasper may be disposed between the second ends of the arms.

In various embodiments, the present disclosure relates to a tissue clipping device. The device may include a housing defining a cavity and may have a first end that is movable toward a second end of the housing within the cavity. A plurality of arms extending from a first end to a second end may be received within the cavity. The arms may be movable between an open configuration, in which the second ends of the arms may be separated apart from one another, and a closed configuration, in which the second ends of the arms may be displaced toward one another. An inner layer may be disposed about the piston housing and may extend proximally of the housing to define a chamber configured to contain a fluid. The chamber may be compressible from a plurality of angles relative to a longitudinal axis of the clipping device in response to an application of a compressive force. In response to an application of a compressive force to the chamber, the first end of the housing may be moved toward the second end of the housing extending the arms to the open configuration. When the compressive force is not applied to the chamber, the first end of the housing may be displaced away from the second end of the housing retracting the arms to the closed configuration.

In the described and other embodiments, an outer layer may be disposed about the inner layer, and the outer layer may be configured to be grasped from a plurality of angles relative to a longitudinal axis of the clipping device to apply the compressive force to the chamber. The inner layer may be configured to be grasped from a plurality of angles relative to a longitudinal axis of the clipping device to apply the compressive force to the chamber. The arms may be formed of a single wire bent at a medial portion. The medial portion may form the first ends of the arms. The arms may be biased to the open configuration.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1:
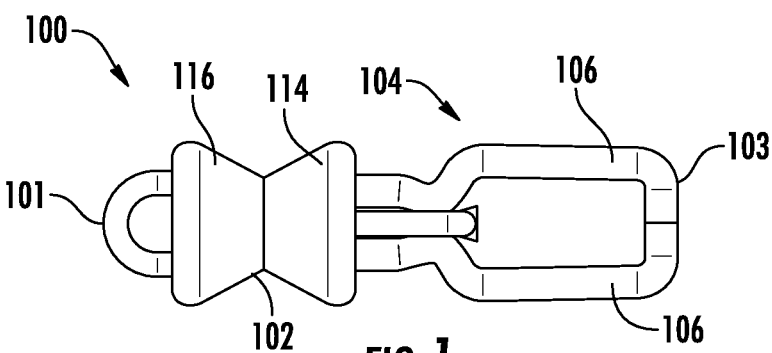
FIG. 1 shows a top view of a clip device, according to an embodiment of the present disclosure, in a closed configuration.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with reference to particular body lumens and tissues, it should be appreciated that such devices, systems, and methods may be used with a variety of anatomies that include the gastrointestinal tract, the bronchi, mucosal tissue, epithelial tissue, connective tissue, muscle tissue, and the like.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional along a medical device when introducing the device into a patient, while the term "proximal" refers to the end closest to the medical professional along the medical device when introducing the medical device into a patient.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

As used herein, the terms "element" and "member" may be used interchangeably among and between the description of the figures, discussion of various embodiments, and in the claims.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

The present disclosure may be further understood with reference to the following description and the appended drawings, wherein like elements are referred to with the same reference numerals. The present disclosure relates to a clip opening mechanism of an endoscopic tissue traction device for, in an example, endoscopic submucosal dissection (ESD) and/or endoscopic mucosal resection (EMR). Exemplary embodiments of the present disclosure describe a clip device including an opening mechanism that allows a physician to open and reposition the clip device from any angle. In these embodiments, the physician is able to grasp the opening mechanism of the clip device from any approach angle and open the clip for attaching to tissue. In exemplary embodiments of the present disclosure, two clip devices may be used in conjunction with a tether to form a tether traction clip device.

In various embodiments, the clip devices described herein may be used interchangeably in systems in a substantially similar manner. Various clip devices may have one or more gripping elements or members that may move with respect to each other such that the device and/or system transitions between an open configuration and a closed configuration. It will be understood that the gripping elements or members described with respect to a specific embodiment may be used additionally or interchangeably with that of another embodiment in a substantially similar manner.

Tether traction clip devices may be used to manipulate the flap of tissue during ESD. However, these clip devices may be difficult to open, close, and/or position, because the clip devices may require gripping along a specific angle or plane. Other tissue clipping devices, e.g., a tissue traction device for ESD, may include an opening mechanism to engage and manipulate tissue. Operating such devices may be difficult for a medical professional because of the viewing angle, devices or anatomies blocking the field of view, size of the operating tools, or strict angles of proper engagement with respect to the devices, as examples. For example, a clipping device may be engaged by another instrument controlled by a medical professional to orient the device and/or manipulate the arms of the device. The device may be controlled during a procedure as above by engaging the device substantially along the longitudinal axis of the device. Attempts to engage the device at angles that are not substantially along the longitudinal axis may fail to control the device properly, cause procedural errors or delay, or frustrate the medical professional. Thus, it is with these considerations in mind that the present improvements may be helpful to allow a physician to open, close and/or reposition a clip from numerous angles.

Figure 2:
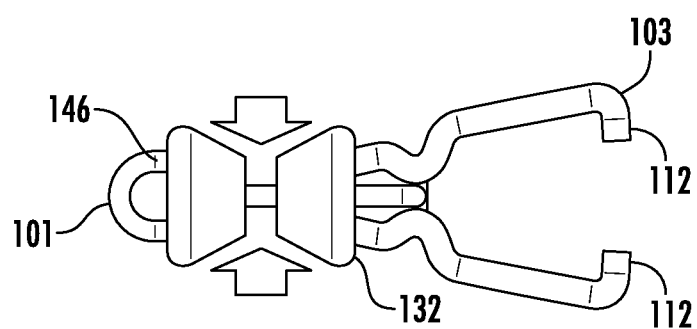
FIG. 2 shows a top view of the clip device of FIG. 1 in an open configuration.
Figure 3:
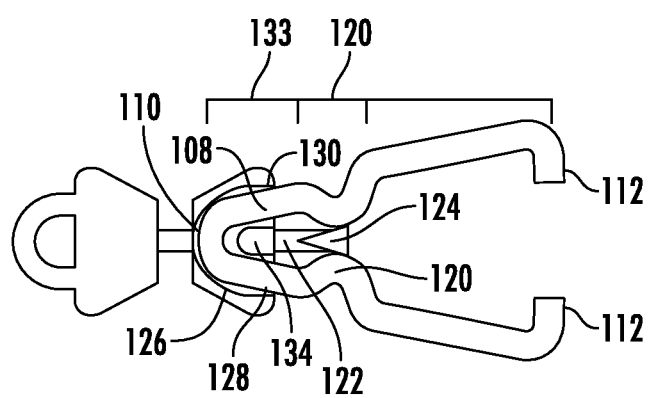
FIG. 3 shows a partial cross-sectional view of the clip device of FIG. 2.
Figure 4:
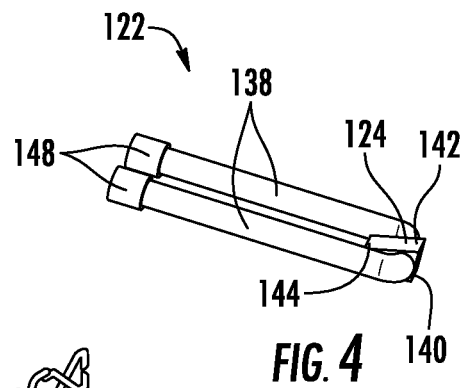
FIG. 4 shows a perspective view of a cam member of the clip device of FIG. 1, according to an embodiment of the present disclosure.
Figure 5:
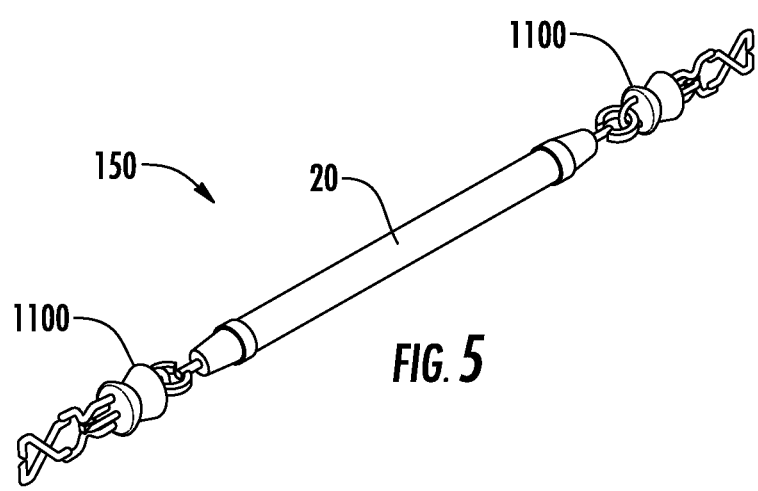
FIG. 5 shows a perspective view of a tether traction clip system according to an embodiment of the present disclosure.
Figure 6:
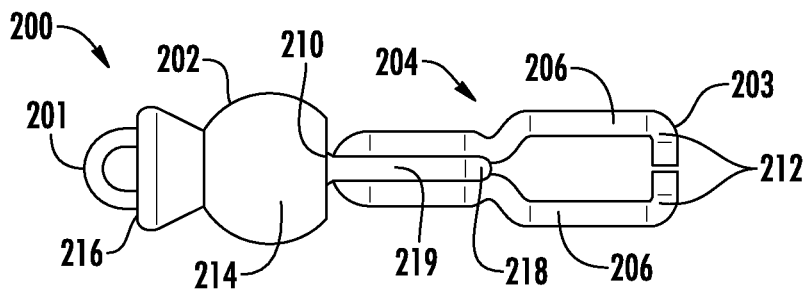
FIG. 6 shows a top view of a clip device, according to an embodiment of the present disclosure, in a closed configuration.

As shown in FIGS. 1-4, a clip device 100 according to an exemplary embodiment of the present disclosure extends from a coupling end 101, which is configured to couple to a tether 20 (e.g., in a similar fashion as shown in FIG. 5 with respect to device 1100 FIGS. 11A-11D), to a clipping end 103 opposite the coupling end 101. The clip device 100 comprises a grasping portion 102 and a clipping portion 104 and is insertable through, for example, a working channel of a flexible endoscope to a target tissue to be treated. The grasping portion 102 comprises first and second conical gripping elements 116, 114 and a cam member 122. The clipping portion 104 includes clip arms 106. The clip device 100 is sufficiently flexible to permit it to traverse a tortuous path through the body, e.g., passing through the working channel of an endoscope inserted through a natural body lumen accessed via a natural bodily orifice. The clipping portion 104 includes clip arms 106 which, in this embodiment, are formed from a single wire 108. As can be seen in FIG. 3, the wire 108 is bent at a medial portion to form a first end 110 of the clip arms 106, the first end 110 being closest to the coupling end 101 of the clip device 100. The first and second clip arms 106 each extend from the first end 110 to second ends 112 at the clipping end 103 of the clip device 100. The clip arms 106 can be moved between an open configuration, in which the second ends 112 of the clip arms 106 are separated from one another to receive target tissue therebetween, and a closed configuration, in which the second ends 112 of the clip arms 106 are moved toward one another e.g., to grip the target tissue therebetween or to reduce an overall size of the device compared to when the clip arms 106 are moved apart from one another. The clipping portion 104 of the clip device 100 is coupled to the grasping portion 102 via the second conical gripping element 114. The clip arms 106 are movable between the open and closed configuration via movement of the second conical gripping element 114 relative to the first conical gripping element 116. The coupling end 101 of the clip device 100 of this embodiment is configured to be coupled to a tether 20 (depicted in FIGS. 22-25), as will be described in further detail below.

As further shown in FIG. 3, the clip arms 106 are joined at the first end 110 and extend to second ends 112. As those skilled in the art will understand, the clip arms 106 of this embodiment are biased toward the closed configuration. When the grasping portion 102 of the clip device 100 is activated as described below, the clip arms 106 are forced into the open configuration. Each of the clip arms 106 of this embodiment is contoured to include a spring portion 120 formed as a curve or bend in the clip arms 106 that extends toward a longitudinal axis of the clip device 100. The spring portions 120 form a space therebetween that is sized and shaped to receive a first end of the cam member 122 of the gripping portion 104. The cam member 122, which includes, in this embodiment, a triangular wedge 124 at the first end thereof, deflects the clip arms 106 away from one another to the open configuration as it is advanced between the clip arms 106 toward the first end 110 of the clip arms 106.

The gripping portion 102 includes the first gripping element 116 (i.e., closer to the coupling end 101 of the clip device 100) and a second gripping element 114 (i.e., closer to the clipping end 103 of the clip device 100) and the cam member 122 with the wedge 124. In this embodiment, the first and second gripping elements 116, 114 are substantially conical (e.g., frustroconical) with a diameter that increases as a distance from ends at which the first and second gripping elements 116, 114, respectively, abut one another, increases. As shown in FIG. 1, each of the first and second gripping elements 116, 114 tapers toward a minimum diameter at the ends positioned adjacent to one another forming an hourglass shape when the first and second gripping elements 116, 114 abut one another. Specifically, the first gripping element 116 tapers from a first end thereof to a second end while the distal gripping element 114 tapers from a second end thereof to a first end (the first end being adjacent to the second end of the first gripping element 116). This hourglass shape is used as a gripping cylinder which allows the user to grip the clip device 100 (e.g., using a gripper tool 10 (depicted in FIG. 28) inserted via a working channel of a flexible endoscope) regardless of the clip orientation relative to the endoscope. As also illustrated in FIG. 3, the second gripping element 114 includes a curved channel 126 therein that extends from a first end 128 to a second end 130, the first and second ends 128, 130 being open at the second end 132 of the distal gripping element 114. The channel 126 is sized and shaped to receive a first portion 133 of the clip arms 106, extending between the first end 112 and the spring portion 120, therethrough. A surface or ledge 134 of the second end of the second gripping element 114 between the open first and second ends 128, 130 of the curved channel 126 is positioned between the first portion 133 of the clip arms 106 to provide a stop controlling a maximum opening of the clip arms 106 and preventing the clip arms 106 from passing out of the second gripping element 114. The second gripping element 114 also includes two through holes (not shown) extending from the first end to the second end of the distal gripping element 114, each through hole being configured to receive a leg 138 of the cam member 122.

The cam member 122 of this embodiment, as shown in FIG. 4, is substantially U-shaped with two legs 138 extending toward the coupling end 101 from a distal U-bend 140. Each of the legs 138 includes an enlarged stop member 148. The wedge 124 is centrally positioned at the U-bend and is substantially triangular in shape. Specifically, the wedge 124 tapers from a second end 142 closest to the clipping end 103 to a first end 144 closest to the coupling end 101. The wedge 124 extends toward the coupling end 101 from the U-bend 140 between the two legs 138. The legs 138 of the cam member 122 are slidably received through the through holes (not shown) within the first gripping element 116. The blind holes extend partially through the length of the first gripping element 116 a distance equal to a length of the stop members 148. The blind holes have a diameter substantially equal to the stop members 148. However, the openings of the blind holes at the second end of the first gripping element 116 have a smaller diameter (i.e., a diameter equal to a diameter of the clip arms 106) such that the stop members 148 of the cam member 122 are prevented from passing out of the first gripping element 116. Thus, the first gripping element 116 and the cam member 122 are immovable with respect to one another. It is noted that the first ends of the cam member 122 may be coupled to the first gripping element 116 in any other preferred method, such as adhesion, welding, etc., so long as the components do not move relative to each other.

In use, when the clip device 100 is in the closed configuration, the spring portions 120 of the clip arms 106 are spaced a distance smaller than a width (i.e., a dimension extending in a plane perpendicular to the longitudinal axis of the clip device 100 between the two clip arms 106) of the wedge 124 of the cam member 122. As a radially inwardly directed force (i.e., a gripping force) is applied by, for example, a gripper tool 10 (see e.g., FIG. 26), at the tapered ends of the first and second gripping elements 116, 114, the first and second gripping elements 116, 114 are displaced relative to one another (i.e., moved away from one another along the longitudinal axis of the clip device 100), as shown in FIG. 2. This linear motion actuates the cam member 122 such that the wedge 124 moves toward the first end 110 of the clip arms 106 into the space between the spring portions 120, deflecting the spring portions 120 away from one another and moving the clip arms 106 to the open configuration, as shown in FIG. 3. In turn, when the force from the gripper tool 10 is removed from the proximal and distal gripping elements 116, 114, due to the spring action of the clip arms 106 against the triangular surface of the wedge 124, the cam member 122 is forced to its original location, drawing the clip arms 106 toward one another into the tissue gripping configuration gripping any tissue received between the second ends 112 of the clip arms 106.

Figure 7:
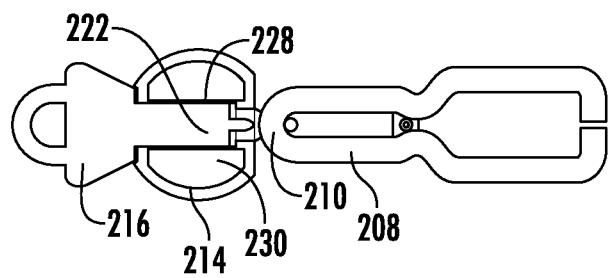
FIG. 7 shows a partial cross-sectional view of the clip device of FIG. 6 in a closed configuration.
Figure 8:
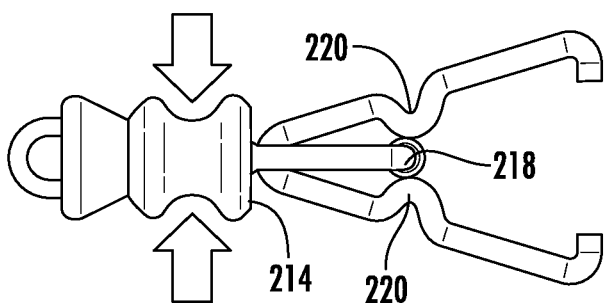
FIG. 8 shows a top view of the clip device of FIG. 6 in an open configuration.

As shown in FIGS. 6-10, a clip device 200 according to an exemplary embodiment of the present disclosure is substantially similar to the clip device 100, except as described herein. Specifically, the clip device 200 extends from a coupling end 201 to an opposing clipping end 203 and includes a grasping portion 202 and a clipping portion 204. The clip device 200 is insertable through, for example, a working channel of an endoscope to target tissue to be treated. The clipping portion 204 includes clip arms 206 which, in this embodiment, are formed from a single wire 208, as shown in FIG. 7. As can be seen in FIG. 7, the wire 208 is bent at a medial portion to form a first end 210 of the clip arms 206 closest to the coupling end 201. The clip arms 206 extend from the first end 210 to second ends 212 located at the clipping end 203 of the clip device 200. The clip arms 206 are biased to a closed configuration but each include curved portions forming spring portions 220, similar to spring portions 120.

Figure 10:
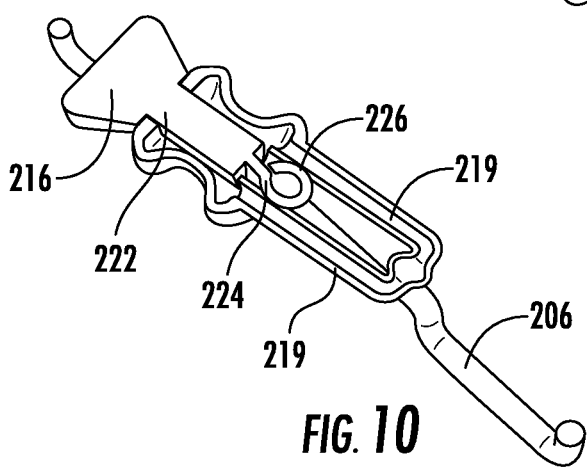
FIG. 10 shows another cross-sectional view of the clip device of FIG. 6.

The grasping portion 202 includes a conical gripping element 216, a fluid chamber 214, a distal balloon chamber 218 and two connection channels 219. The conical gripping element 216 is substantially similar in shape to the first conical gripping element 116 except that it includes an extension 222 extending in the direction of the clipping end 203, as can be seen in FIG. 7. The extension 222 is configured to extend through a central lumen 228 of the fluid chamber 214. A second end 224 (closest to the clipping end 203) of the distal extension 222 extends past a second end (closest to the clipping end 203) of the fluid chamber 214 to couple to the first end 210 of the clip arms 206, as shown in FIG. 10. In the present embodiment, the second end 224 of the distal extension 222 is a hook or loop 226 defining a central space sized and shaped to receive the first end 210 of the clip arms 206 therethrough.

Figure 9:
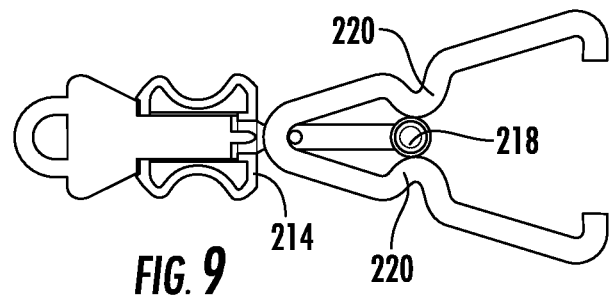
FIG. 9 shows a partial cross-sectional view of the clip device of FIG. 6 in an open configuration.

The fluid chamber 214, is substantially spherical in shape with the closed lumen 228 extending therethrough from a first end to a second end thereof. The fluid chamber 214 includes an internal cavity 230 configured to be filled with a fluid such as, for example, saline, sterile water, gel, or any other minimally compressible fluid appropriate for use in internal medicine. The fluid chamber 214 is formed of a deformable material such as, for example, nylons, PEBAX, polyethylene terephthalate (PET), rubber, or silicone, such that when and external pressure is applied thereto by, for example, a gripper tool 10, the fluid chamber contracts inwardly, reducing and internal volume and dispelling fluid therefrom into the connection channels 219. The connection channels 219 extend from the fluid chamber 214 to the balloon chamber 218 and provides fluid communication therebetween. That is, fluid that is forced out of the fluid chamber 214, upon application of an external force, moves through the connection channels 219 and into the balloon chamber 218. The balloon chamber 218 is inflatable from a normal deflated state, shown in FIG. 7, as the balloon chamber 218 is filled with fluid. The balloon chamber 218 is positioned between the spring portions 220 of the clip arms 206 so that as fluid is forced thereinto, the balloon chamber 218 inflates, generating enough pressure to open the clip arms 206, as shown in FIG. 9. When the external force is removed from the fluid chamber 214, the spring portions 220 apply an inward force on the balloon chamber 218, reducing the internal volume of the balloon chamber 218 so that the fluid moves back through the connection channels 219 and into the fluid chamber 214.

In the embodiment described above in FIGS. 6-10 or otherwise within the scope of the present disclosure, various of the clip devices may have one or more chambers that may be engaged and disengaged, such that the one or more chambers may be compressed or inflated to transition the devices between a tissue receiving configuration and a tissue engaging configuration. It will be understood that the chambers described with respect to a specific embodiment may be used additionally or interchangeably with that of another embodiment in a substantially similar manner.

Figure 11A:
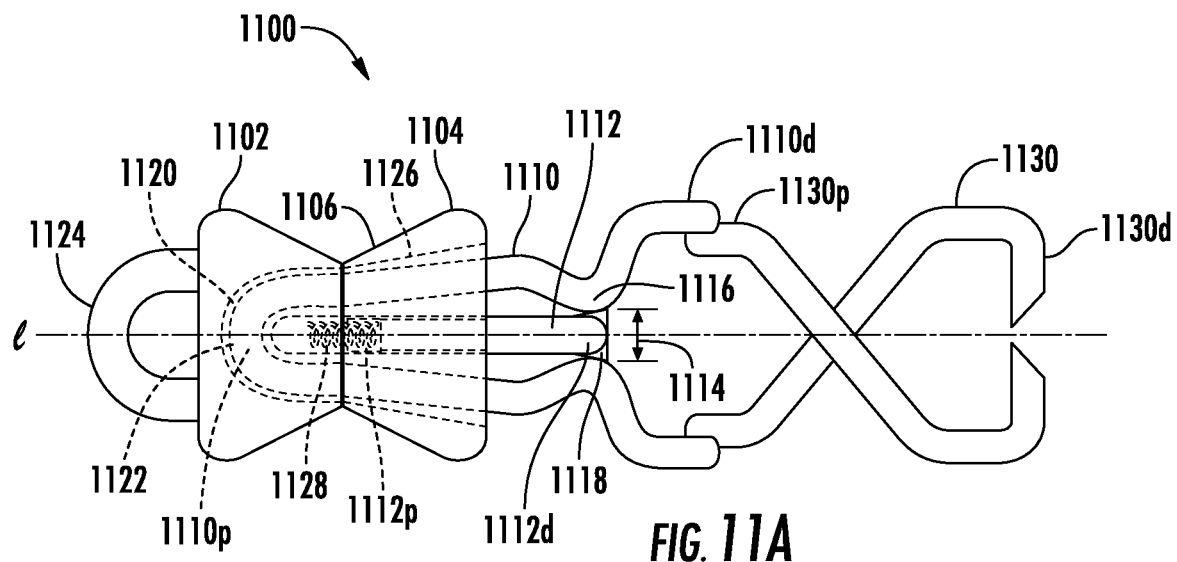
FIG. 11A shows a top view of a tissue clipping device in a closed configuration, according to an embodiment of the present disclosure.
Figure 11B:
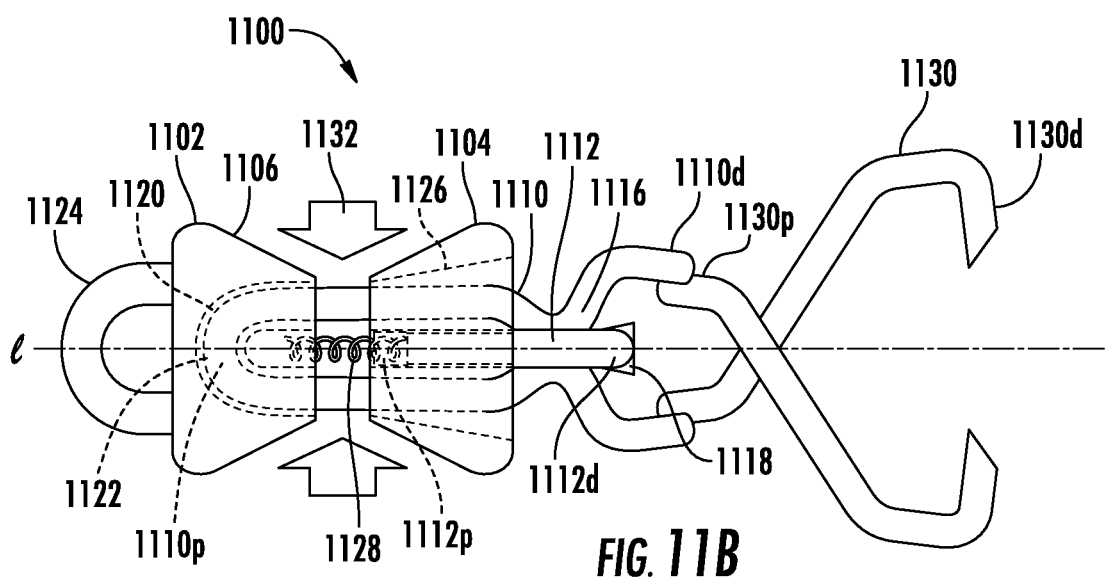
FIG. 11B shows a top view of the device of FIG. 11A in an open configuration.
Figure 11C:
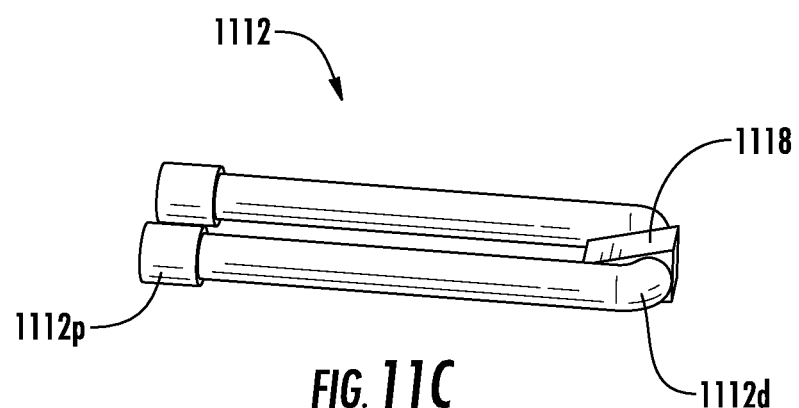
FIG. 11C shows a perspective view of a cam member of the device of FIGS. 11A and 11B.
Figure 11D:
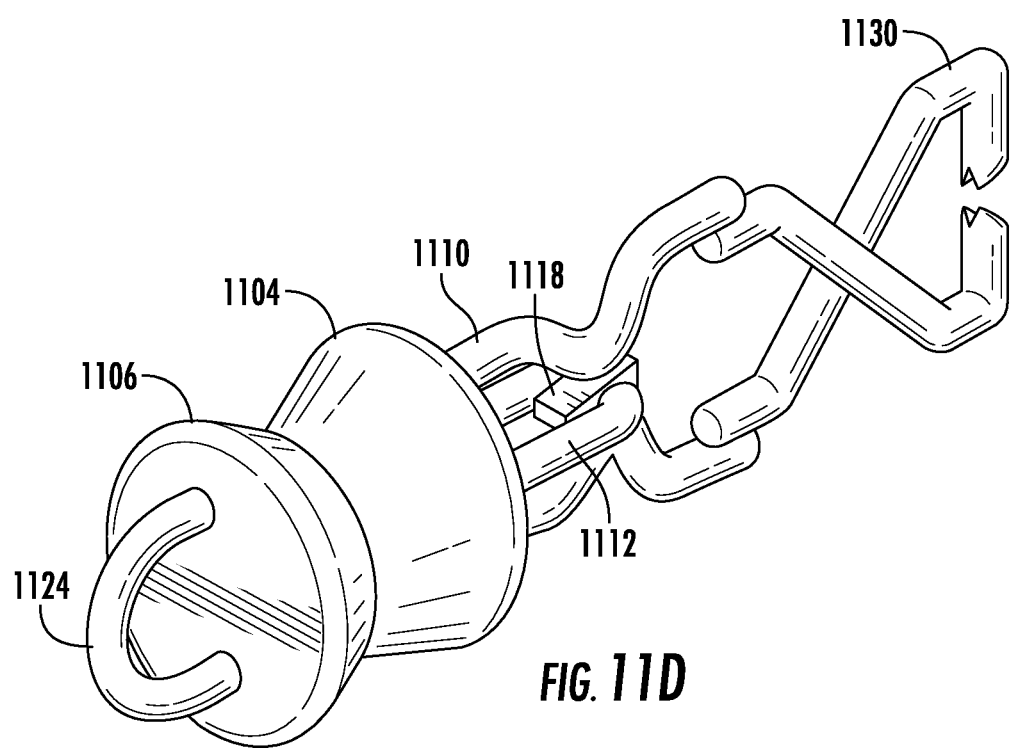
FIG. 11D shows an isometric view of the device of FIGS. 11A and 11B.

With reference to FIGS. 11A-11D, an embodiment of a tissue clipping device 1100 is illustrated, which includes a first member 1102 and second member 1104 that are a substantially frustum shape. Two clip arms 1110 extend from a first end 1110$p$ to a second end 1110$d$. The first end 1110$p$ of each arm 1110 is received within the first member 1102 via a channel 1120 extending through the first member 1102. The clip arms 1110 are formed of a single wire that is bent at a medial portion 1122 that forms the first ends 1110*p* of the arms 1110. A grasper 1130 for engaging tissue is engaged (e.g., held) between the second end 1110*d* of the arms 1110. The grasper 1130 has a first end 1130*p* between the arms 1110 and a second end 1130*d* comprising jaws for engaging tissue. The grasper 1130 has first and second grasper arms that are in a crossing configuration. A spring force in a bend at the medial portion 1122 of the clip arms 1110 contained in the first member 1102 creates a bias at the second end 1110*d* of the clip arms 1110 urging the arms toward each other, such that the spring portion 1116 of arms 1110 are driven toward each other, e.g., to be in substantial contact with one another. The grasper 1130 assumes an open configuration when first member and second member 1102, 1104 are spread apart (e.g., FIG. 11B). The spring force could be applied by a torsion spring, a flat spring or the like. The clip arms 1110 are movable such that the grasper 1130 may transition between a closed configuration (e.g., for deployment and/or engaging tissue), as depicted in FIG. 11A, in which the spring portions 1116 of the clip arms 1110 are separated apart from one another, and an open configuration (e.g., for receiving tissue), as depicted in FIG. 11B, in which the spring portions 1116 of the clip arms 1110 are in contact with one another. The spring portion 1116 of each of the arms 1110 forms a spring space 1114 between the spring portions 1116. The spring space 1114 is open when the device 1100 is in the closed configuration (FIG. 11A), and the spring space 1114 is closed when the device 1100 is in the open configuration (FIG. 11B). The second member 1104 is slidably positioned about the plurality of arms 1110. The arms 1110 extend through tapered channels 1126 of the second member 1104. Each of the first member 1102 and the second member 1104 may be grasped either individually or together from a plurality of angles relative to a longitudinal axis E of the clipping device 1100. The first and second members 1102, 1104 may each be displaced apart relative to one another along the longitudinal axis E of the clipping device 1100 into the open configuration in response to an application of a compressive force 1132. A cam member 1112 extends from a first end 1112*p* to a second end 1112*d*. The first end 1112*p* of the cam member 1112 is fixedly coupled to the second member 1104 and the second end 1112*p* extends into and engages the spring space 1114 in the closed configuration. The cam member 1112 is moved out of engagement with the spring space 1114 when the first and second members 1102, 1104 are displaced relative to each other to the open configuration, such that as the cam member 1112 is moved out of engagement with the spring space 1114 the spring portions 1116 of the plurality of arms 1110 move toward each other due to the spring force. As such, the arms 1110 cause the grasper jaws 1130 at the second end 1130*d* to move to the open configuration. When the cam member 1112 is engaged between spring portions 1116 in the spring space 1114, the device 1100 is in the closed configuration and the clips arms 1110 are prevented from transitioning the device 1100 to the open configuration while the device 1100 is in a rested state (i.e., without any substantial compressive force 1132 applied). When there is no compressive force 1132 applied, the first and second members 1102, 1104 are displaced towards each other, into substantial contact with one another, e.g., by a linear spring 1128 that extends between the members 1102, 1104. The linear spring 1128 is in a rested state in the closed configuration (FIG. 11A) and is in an extended state (in tension) in the open configuration (FIG. 11B). The extended state of the linear spring 1128 has a spring force that pulls the members 1102, 1104 together, moving the second end 1112*d* of the cam member 1112 into engagement with the spring space 1114 and the spring portions 1116 of the arms 1110. The cam member 1112 includes a U-bend at the second end 1112*d*, two legs extending from the U-bend to the first end 1112*p*, and a wedge 1118 that is centrally positioned on the U-bend at the second end 1112*d*. The wedge 1118 tapers to a smaller width transverse to the longitudinal axis e as the wedge 1118 extends from the U-bend toward the first end 1112*p* between the legs of the cam member 1112. The wedge 1118 is receivable within the spring space 1114. The first and second members 1102, 1104 include angled surfaces 1106 that allow the members 1102, 1104 to move in opposite directions away from each other in response to an application of a compressive force 1132 to the angled surfaces 1106. A loop 1124 extends from the first member 1102 for attachment with another device such as an elastomeric tether.

In an exemplary embodiment, the clip devices 1100 may be coupled to a tether 20 to form a tether traction clip system 150, as shown in FIG. 5. FIG. 5 illustrates a device 1100 as an example, but it will be understood that any embodiment of a clipping device of this disclosure could be used in a substantially similar manner. The tether traction system 150, in this embodiment, comprises two clip devices 1100 coupled together via the tether 20 extending therebetween. Specifically, opposing ends of the tether 20 are coupled to coupling ends 1124 of the clip devices 1100. The tether 20 may be formed of an elastomeric material with high energy recovery properties such as, for example, natural rubber latex, thermoplastic elastomers and silicone rubbers. Alternatively or additionally, the tether 20 may be comprised of a metallic spring or shape memory material. As will be described in further detail below, the tether traction system 150, in this embodiment, allows a physician to adjust a selected portion of tissue to provide the physician with a clearer line of sight to a desired target tissue. For example, a first clip device 1100 may be coupled to a resected portion of tissue while a second clip device 1100 may be coupled to nearby tissue such that the tether 20 provides tension sufficient hold the resected portion of tissue in a desired position.

Figure 12A:
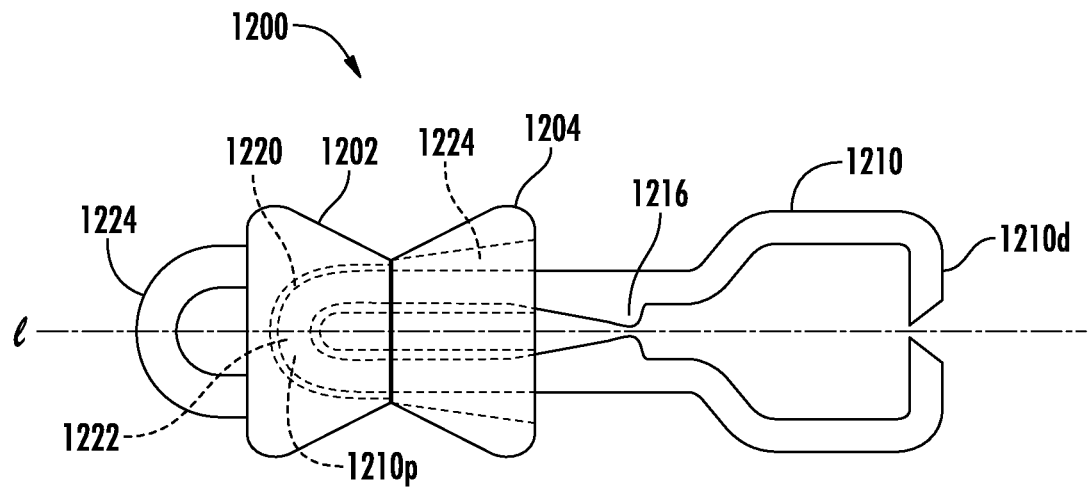
FIG. 12A shows a top view of a tissue clipping device in a closed configuration, according to an embodiment of the present disclosure.
Figure 12B:
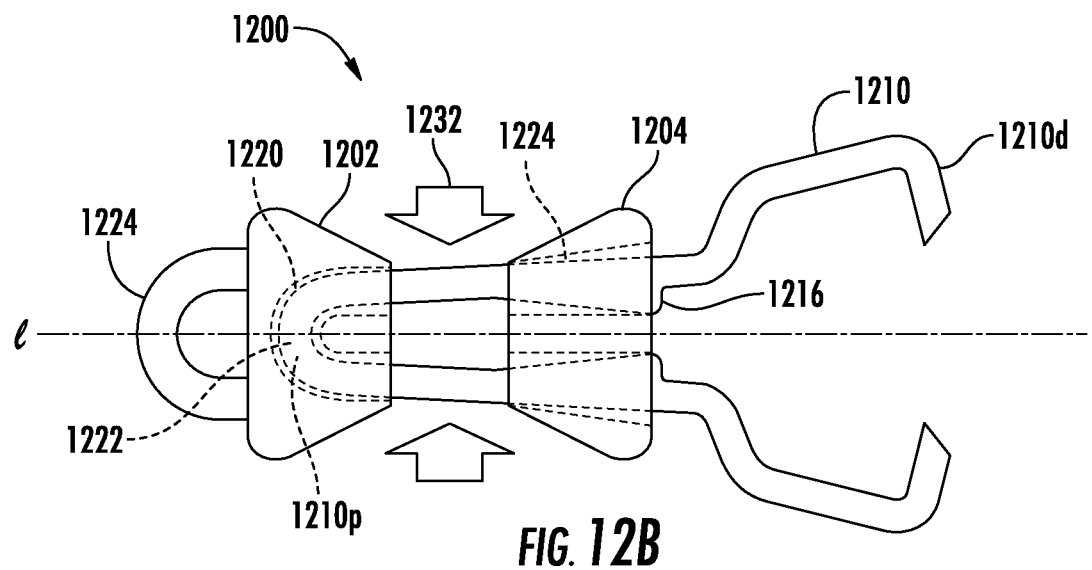
FIG. 12B shows a top view of the device of FIG. 12A in an open configuration.

With reference to FIGS. 12A and 12B, an embodiment of a tissue clipping device 1200 for engaging tissue is illustrated, which includes a first member 1202 that is a substantially frustum shape. Two clip arms 1210 extend from a first end 1210*p* to a second end 1210*d*. The first end 1210*p* of each arm 1210 is received within the first member 1202 via a channel 1220 extending through the first member 1202. The clip arms 1210 are formed of a single wire that is bent at a medial portion 1222 that forms the first ends 1210*p* of the arms 1210. The clip arms 1210 are movable between a closed configuration as depicted in FIG. 12A, in which second ends 1210*d* of the arms 1210 are positioned toward one another, and an open configuration as depicted in FIG. 12B, in which second ends 1210*d* of the arms 1210 are separated away from one another. Each of the clip arms 1210 includes a spring portion 1216 that extends radially toward a longitudinal axis E of the clipping device 1200 and is configured to form a spring space between the spring portions 1216. A spring force in a bend at the medial portion 1222 of the clip arms 1210 contained in the first member 1202 creates a bias at the second end 1210*d* of the clip arms 1210 toward the closed configuration. A second member 1204 is slidably positioned about the plurality of arms 1210, with the arms 1210 extending through tapered channels 1226 of the second member 1204. The tapered channels 1226 each taper (i.e., reduce in diameter) in the direction toward the first member 1202. The tapered channels 1226 are internal to the second member 1204 and are engageable with opposing sloped surfaces of the spring portions 1216 of the arms 1210. The opposing sloped surfaces of the spring portions 1216 of the arms 1210 slope toward each other and the longitudinal axis E, such that when the first and second members 1202, 1204 are displaced apart from one another, the tapered channels 1226 are moved into engagement with the sloped surfaces of the spring portions 1216, separating the arms 1210 apart into the open configuration. When the first and second members 1202, 1204 are displaced into substantial contact with one another, the tapered channels 1226 are moved out of engagement with the sloped surfaces of the spring portions 1216, and the arms 1210 transition to the closed configuration with the spring portion of the arms biased toward each other. Like the first member 1202, the second member 1204 is also a substantially frustum shape. Each of the first member 1202 and the second member 1204 may be grasped either individually or together from a plurality of angles relative to the longitudinal axis E of the clipping device 1200. The first and second members 1202, 1204 may each be displaced relative to one another along the longitudinal axis E of the clipping device 1200 into the open configuration in response to application of a compressive force 1232. The first and second members 1202, 1204 include angled outer surfaces that allow the members 1202, 1204 to move in opposite directions longitudinally away from each other along the longitudinal axis E in response to an application of a compressive force 1232 to the angled outer surfaces. Although the first member 1202 cannot move with respect to the arms 1210 because the end 1210p extends through the first member 1202, the first member 1202 may move away from the second member 1204 together with the arms 1210. When the first and second members 1202, 1204 are displaced relative to each other, the tapered channels 1226 are moved into and out of engagement with the opposing sloped surfaces of the spring portions 1216 of the arms 1210, transitioning the arms 1210 between the closed configuration and open configuration. The second member 1204 or the arms 1210 may move longitudinally with respect to each other while one of the second member 1204 or the arms 1210 are fixed, or both the second member 1204 and the arms 1210 may move longitudinally with respect to each other. The clip arms 1210 are biased to the closed configuration, while the device 1200 is in a rested state (i.e., without any substantial compressive force 1232 applied) with the spring force of the medial portion 1222 biasing the arms 1210 together and the first and second members 1202, 1204 displaced toward each other. A loop 1224 may extend from the first member 1202 for another device to attach or grasp onto (e.g., using a tether therebetween).

Figure 13A:
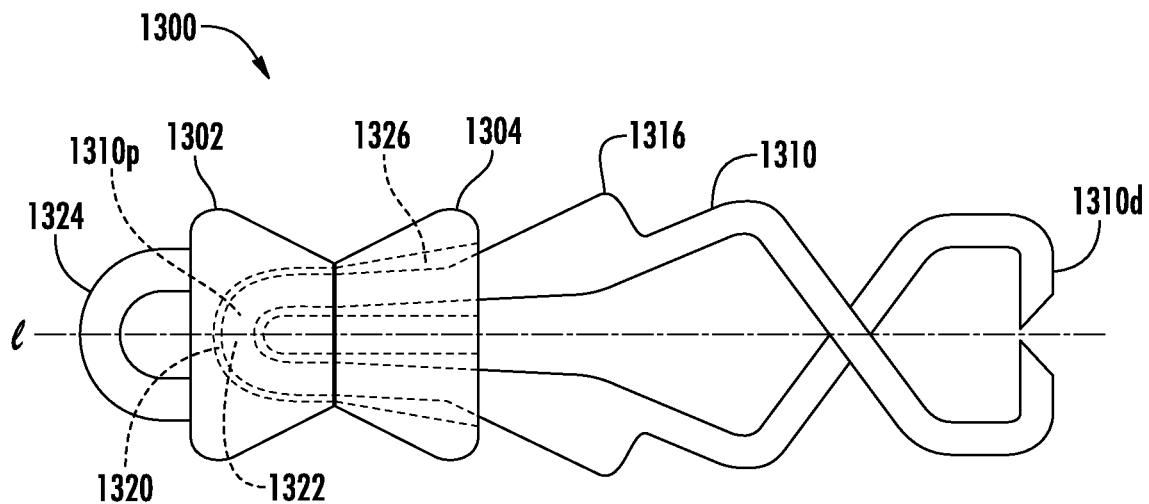
FIG. 13A shows a top view of a tissue clipping device in a closed configuration, according to an embodiment of the present disclosure.
Figure 13B:
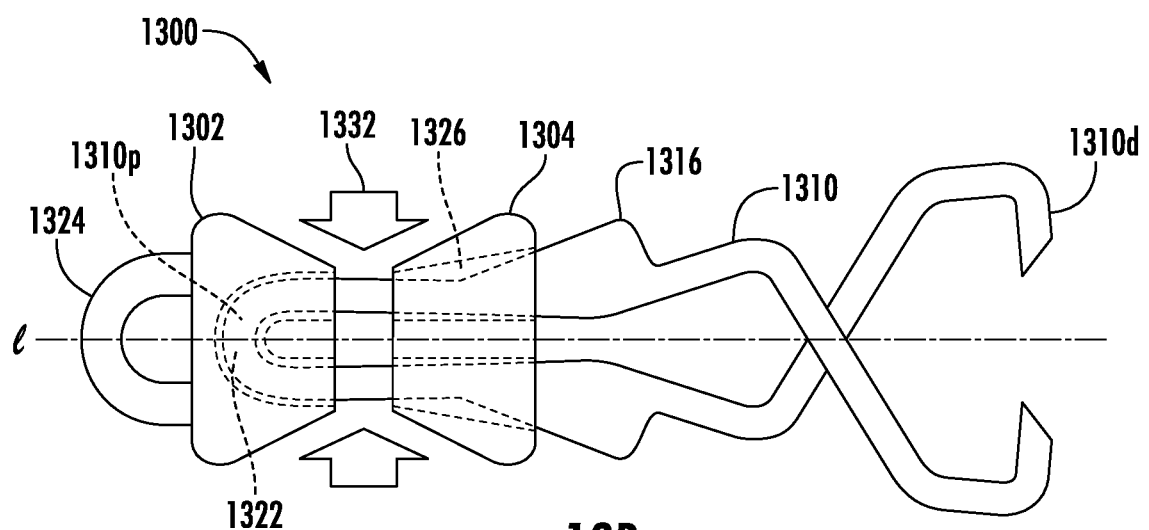
FIG. 13B shows a top view of the device of FIG. 13A in an open configuration.

With reference to FIGS. 13A and 13B, an embodiment of a tissue clipping device 1300 for engaging tissue is illustrated, which includes a first member 1302 that is a substantially frustum shape. Two clip arms 1310 extend from a first end 1310p to a second end 1310d. The first end 1310p of each arm 1310 is received within the first member 1302 via a channel 1320 extending through the first member 1302. The clip arms 1310 are formed of a single wire that is bent at a medial portion 1322 that forms the first ends 1310p of the arms 1310. The clip arms 1310 are movable between a closed configuration as depicted in FIG. 13A, in which second ends 1310d of the arms 1310 are positioned toward one another, and an open configuration as depicted in FIG. 13B, in which second ends 1310d of the arms 1310 are separated away from one another. Each of the clip arms 1310 includes a spring portion 1316 that extends radially away from a longitudinal axis E of the clipping device 1300 and is configured to form a spring space between the arms 1310 at the spring portions 1316. A spring force in a bend at the medial portion 1322 of the clip arms 1310 contained in the first member 1302 creates a bias at the second end 1310d of the clip arms 1310 toward the closed configuration. A second member 1304 is slidably positioned about the plurality of arms 1310 and the arms 1310 extend through tapered channels 1326 of the second member 1304. The tapered channels 1326 each taper (i.e., reduce in diameter) toward the first member 1302. The tapered channels 1326 are internal to the second member 1304 and are engageable with opposing sloped surfaces of the spring portions 1316 of the arms 1310. The opposing sloped surfaces of the spring portions 1316 of the arms 1310 slope away from each other and the longitudinal axis E, such that when the first and second members 1302, 1304 are displaced apart from one another, the tapered channels 1326 are moved into engagement with the sloped surfaces of the spring portions 1316, to transition the arms 1310 apart into the open configuration. When the first and second members 1302, 1304 are displaced into substantial contact with one another, the tapered channels 1326 are moved out of engagement with the sloped surfaces of the spring portions 1316, and the arms 1310 transition to the closed configuration. Like the first member 1302, the second member 1304 is also a substantially frustum shape. Each of the first member 1302 and the second member 1304 may be grasped either individually or together from a plurality of angles relative to the longitudinal axis E of the clipping device 1300. The first and second members 1302, 1304 may each be displaced relative to one another along the longitudinal axis E of the clipping device 1300 into the open configuration in response to application of a compressive force 1332. The first and second members 1302, 1304 include outer angled surfaces that allow the members 1302, 1304 to be displaced in opposite directions away from each other in response to an application of a compressive force 1332 to the outer angled surfaces. Although the first member 1302 cannot move with respect to the arms 1310 because the end 1310p extends through the first member 1302, the first member 1302 may move away from the second member 1304 together with the arms 1310. When the first and second members 1302, 1304 are displaced relative to each other, the tapered channels 1326 are moved into and out of engagement with the opposing sloped surfaces of the spring portions 1316 of the arms 1310 to transition the arms 1310 between the closed configuration and open configuration. The second member 1304 or the arms 1310 may move longitudinally with respect to each other while one of the second member 1304 or the arms 1310 are fixed, or both the second member 1304 and the arms 1310 may move longitudinally with respect to each other. The clip arms 1310 are biased to the closed configuration, while the device 1300 is in a rested state (i.e., without any substantial compressive force 1332 applied) with the spring force of the medial portion 1322 biasing the arms 1310 together and the first and second members 1302, 1304 displaced toward each other. A loop 1313 may be extended from the first member 1302 for another device to attach or grasp onto (e.g., using a tether therebetween).

Figure 14:
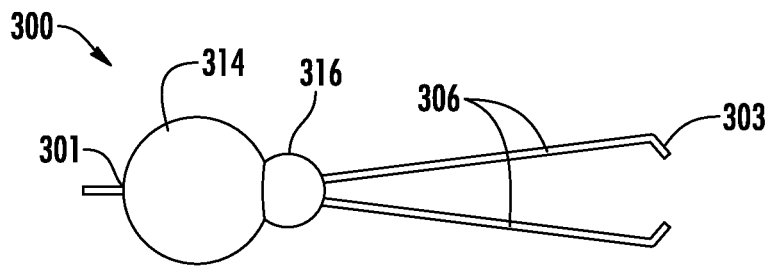
FIG. 14 shows a top view of a clip device, according to an embodiment of the present disclosure, in an open configuration.
Figure 15:
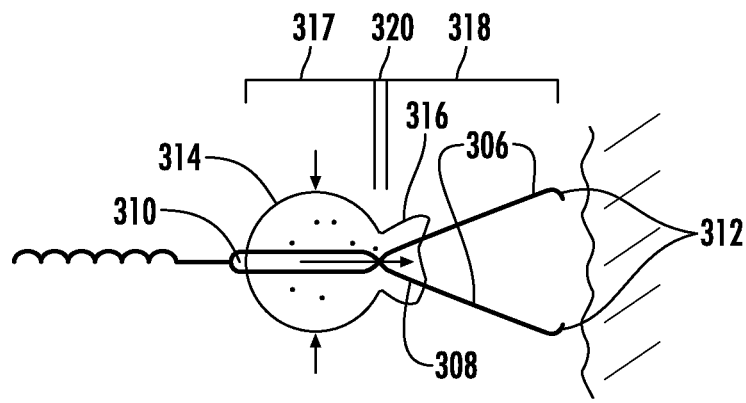
FIG. 15 shows a cross-sectional view of the clip device of FIG. 14.
Figure 16:
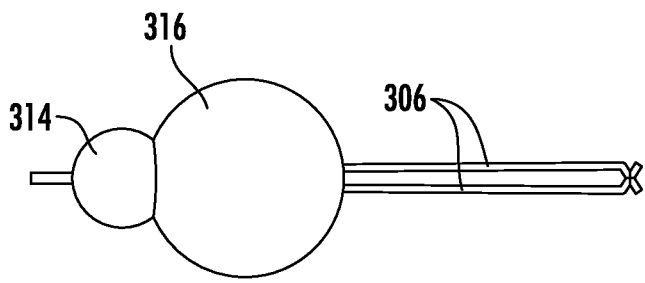
FIG. 16 shows a top view of the clip device of FIGS. 14 and 15 in a closed configuration.
Figure 17:
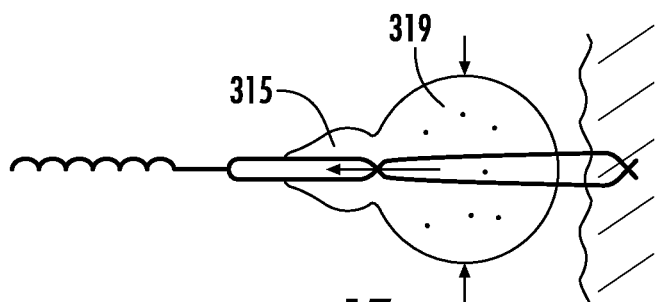
FIG. 17 shows a cross-sectional view of the clip device of FIGS. 14-16 in the closed configuration.

A clip device 300, according to another exemplary embodiment of the present disclosure, is shown in FIGS. 14-17. In this embodiment, the clip device 300 includes a first chamber 314 closest to a coupling end 301 of the clip device 300 and a second chamber 316 closest to an opposing clipping end 303 of the device. The coupling end 301 may be attached to another device, e.g., a tether 20 of FIG. 5, or 27-29. The first and second chambers 314, 316 are connected via a two-way valve such that material or fluid is exchanged therebetween to open and close the clip device 300. In an exemplary embodiment, the material is a memory foam or similar material. In another embodiment, a viscous fluid or similar material may be used. Similar to clip devices 100, 200, the clip device 300 includes first and second clip arms 306 which, in this embodiment, are formed from a single wire 308. As can be seen in FIG. 15, the wire 308 is bent at a medial portion to form a first end 310 of the first and second clip arms 306 which extend therefrom to second ends 312 at the clipping end 303 of the clip device 300. In this embodiment, however, the clip arms 306 are spring-biased to an open configuration. For example, in an embodiment, the clip arms 306 are bent outwardly (i.e., in a direction away from a central longitudinal axis of the clip device 300) at a medial portion thereof. As shown in FIGS. 15 and 17, the clip arms 306 may be bent inwardly (i.e., in a direction toward the central longitudinal axis of the clip device 300) at a spring portion 320 thereof such that the clip arms 306 cross over one another substantially at the central longitudinal axis of the clip device 300. Thus, second portions 318 of the clip arms 306, extending from the spring portion 320 to the second ends 312, will extend away from the central longitudinal axis of the clip device 300 on a side of the central longitudinal axis that is opposite first portions 317 of the clip arms 306, extending from the first end 310 to the spring portion 320.

The clip arms 306 are disposed within the dual chambers with the first portions 317 disposed within the proximal chamber 314 and the second portions 318 partially disposed within the second chamber 316 and partially extending past a second end of the second chamber 316 closest the clipping end 303, as can be seen in FIG. 15. The first and second chambers 314, 316 are substantially spherical in shape and include internal cavities 315, 319, respectively, configured to hold the memory foam material. The first and second chambers 314, 316 are formed of a deformable material which allows the first and second chambers 314, 316 to inflate and deflate as a result of material passing therebetween. As noted above, the first and second chambers 314, 316 are coupled to one another via a two-way valve which allows free movement of the fluid between the two chambers 314, 316. Thus, for example, when an external pressure is applied to the first chamber 314 by, for example, a gripper tool 10, the first chamber 314 contracts inwardly, reducing and internal volume and dispelling fluid therefrom into the second chamber 316. Contrarily, when an external pressure is applied to the second chamber 316 by the gripper tool 10, the second chamber 316 contracts inwardly, reducing the internal volume and dispelling fluid therefrom into the first chamber 314. Alternatively, a contracting force applied by the material of the first chamber 314 may be greater than that provided by the material of the second chamber 316 so that, when the grasper is released from the second chamber 316, the first chamber 314 contracts automatically forcing the material out of the first chamber 314 and into the second chamber 316, automatically drawing the clip arms 306 together into the tissue gripping configuration.

In use, the clip arms 306 are moved to the closed configuration, depicted in FIG. 16, for insertion by squeezing the first chamber 314 until the material therein is moved to the second chamber 316, as shown in FIG. 15. This movement of the material to the second chamber 316 forces the clip arms 306 to the closed configuration by inflating the second chamber 316 laterally of the second portions 318 clip arms 306. This inflation of the second chamber 316 pushes the clip arms 306 towards one another and into the closed, tissue gripping configuration. Once the clip device 300 has been positioned at a target site adjacent target tissue, the gripper tool 10 is used to apply pressure to the second chamber 316, as shown in FIG. 17, forcing the material to move back into the first chamber 314. With the pressure removed from the second portions 318 of the clip arms 306, the clip arms 306 move under their pre-configured bias to the open configuration as shown in FIG. 14. Clip ends 312 of the clip arms 306 are then positioned on either side of the target tissue and the clip arms 306 are again moved to the closed configuration by applying pressure to the first chamber 314 using the gripper tool 10, clipping the target tissue.

Figure 18A:
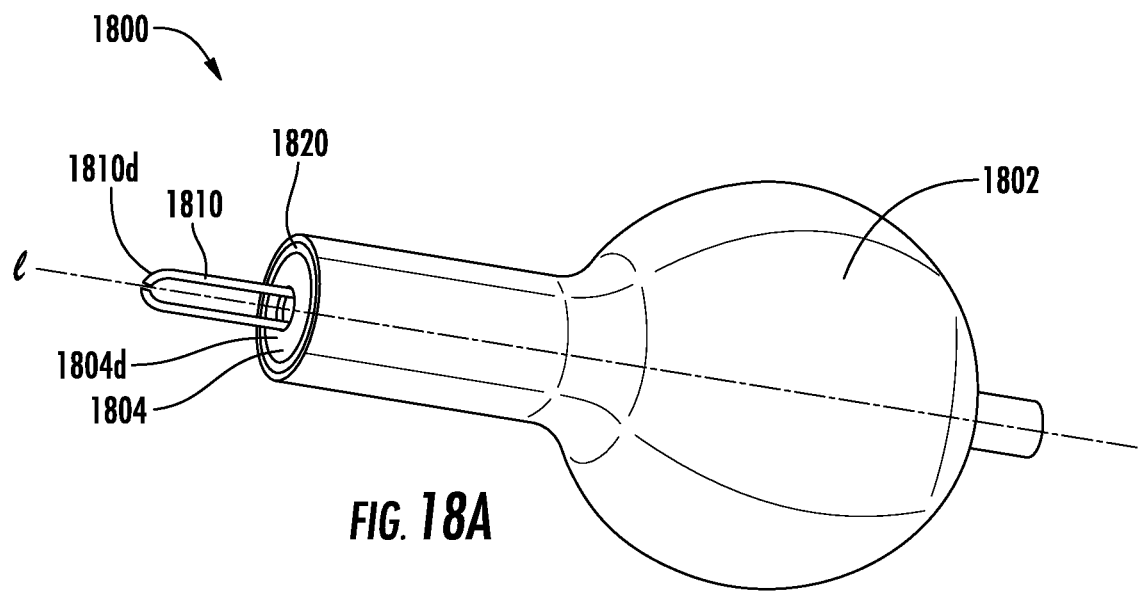
FIG. 18A shows an angled view of a tissue clipping device in a closed configuration, according to an embodiment of the present disclosure.
Figure 18B:
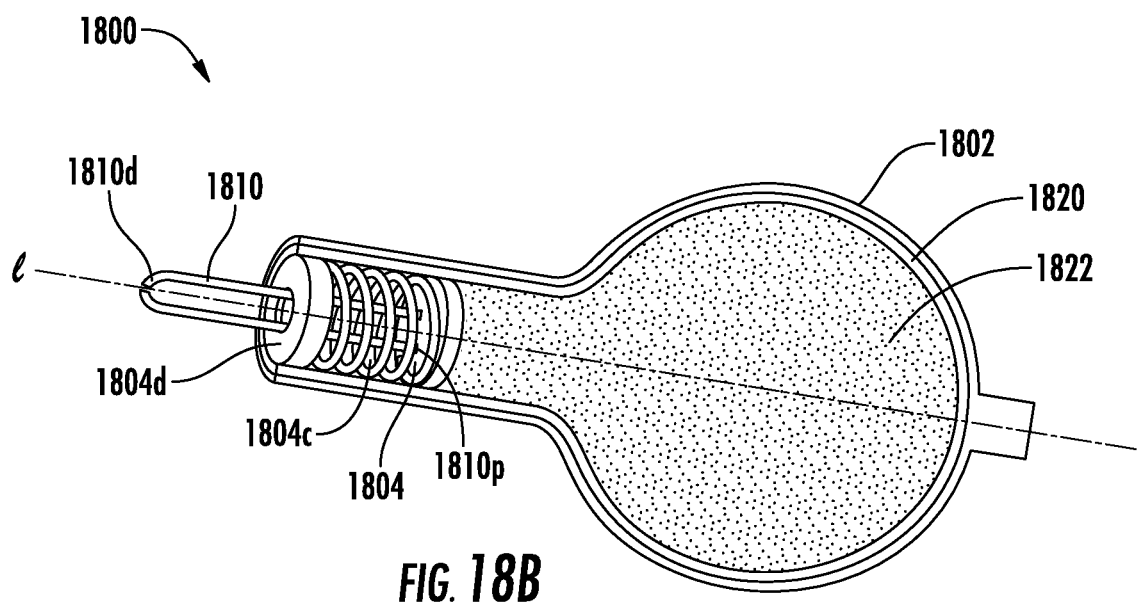
FIG. 18B shows an internal view of the tissue clipping device of FIG. 18A in the closed configuration.
Figure 18C:
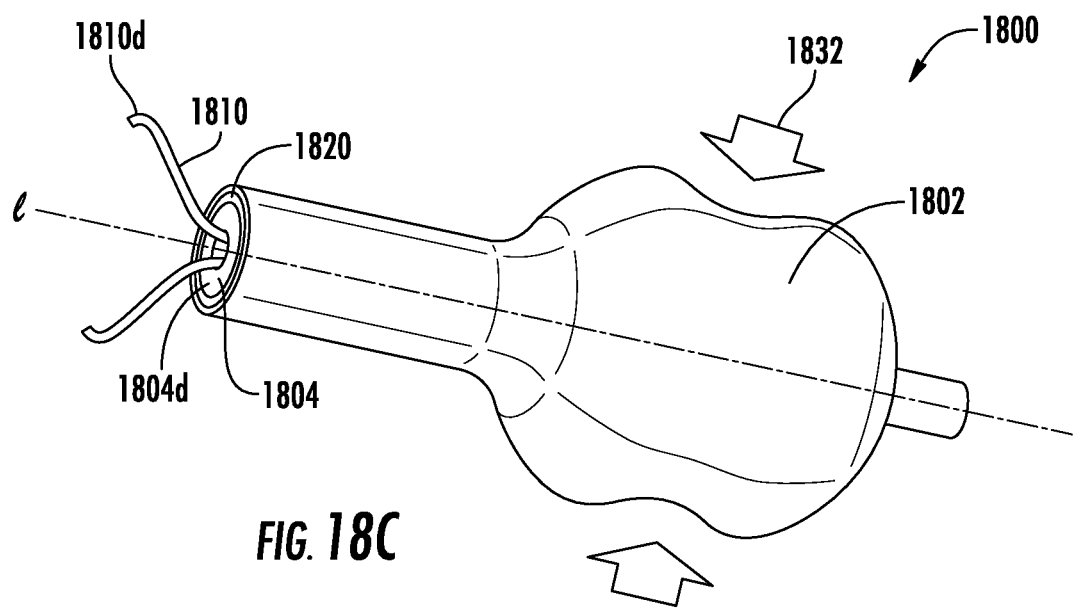
FIG. 18C shows an angled view of the device of FIGS. 18A and 18B in an open configuration.
Figure 18D:
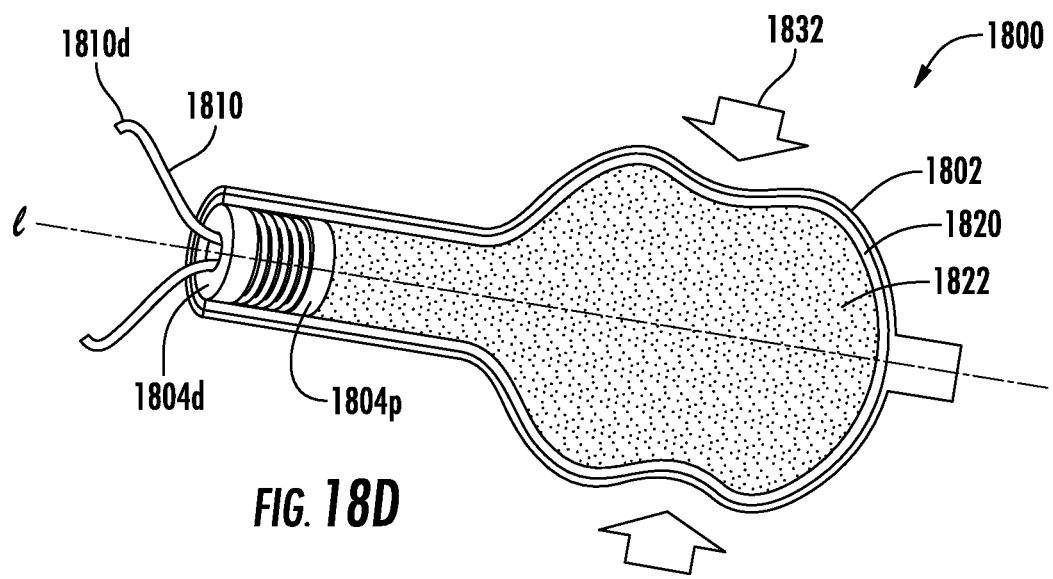
FIG. 18D shows an internal view of the tissue clipping device of FIGS. 18A-18C in the open configuration.

With reference to FIGS. 18A-18D, an embodiment of a tissue clipping device 1800 for engaging tissue is illustrated. FIGS. 18A and 18B illustrate the device 1800 in closed configuration, while FIGS. 18C and 18D illustrate the device 1800 in an open configuration. FIGS. 18B and 18D are partial cross-sectional views of the device 1800 with portions removed/revealed. The device 1800 includes a housing 1804 defining a cavity 1804c having a first end 1804p movable toward a second end 1804d within the cavity 1804c. Within the cavity 1804c are two clip arms 1810 that extend from a first end 1810p to a second end 1810d. The first end 1810p of each arm 1810 is received within the cavity 1804c. The clip arms 1810 are movable between an open configuration (e.g., as illustrated in FIGS. 18C and 18D), in which second ends 1810d of the arms 1810 are separated apart from one another, and a closed configuration (e.g., as illustrated in FIGS. 18A and 18B), in which second ends 1810d of the arms 1810 are displaced toward one another. The arms 1810 are biased in the open configuration or shaped in a fashion such that when they extend out of the cavity 1804c of the housing 1804 and mostly past the second end 1804d, the arms 1810 move into the open configuration. It is the second end 1804d of the housing 1804 that restrains the arms 1810 into the closed configuration. A spring element is contained in the cavity 1804c of the housing 1804 that biases the ends 1804p, 1804d away from each other into the closed configuration when the spring element is in a relaxed configuration. The housing 1804 is within an inner layer 1820. The inner layer 1820 extends proximally of the housing 1804 into a chamber 1822 that contains a fluid. The inner layer 1820 may be compressed by a force 1832 from a plurality of angles relative to a longitudinal axis E of the clipping device 1800 into the open configuration. When compressed, the inner layer 1820 forces the fluid 1822 against the first end 1804p of the housing 1804 such that the first end 1804p is moved toward the second end 1804d of the housing 1804. When the compressive force 1832 is not applied to the layers 1802, 1820 and the chamber 1822, the first end 1804p of the housing 1804 is displaced away from the second end 1804d of the housing 1804, retracting the arms 1810 to the closed configuration. As the ends 1804p, 1804d of the housing move toward each other, the second ends 1810d of the arms 1810 move away from one another to the open configuration. An outer layer 1802 is layered over the inner layer 1820 and, like the inner layer 1802, may be grasped from a plurality of angles relative to a longitudinal axis E. The inner layer 1820 may comprise a flexible and compliant material while the outer layer 1802 may comprise a more rigid and less compliant yet flexible material relative to the inner layer 1820. Examples of materials comprising the inner layer 1802 include thermoplastic elastomers (TPE) with low durometer, polyisoprene, nitrile, polysiloxane. Examples of materials comprising the outer layer 1802 include materials resistant to puncture such as polyurethane, thermoplastic urethane elastomers, and polyester amide elastomers, copolyether ester elastomers. The arms 1810 may be formed from a single wire bent at a medial portion at the first end 1810p.

Figure 19:
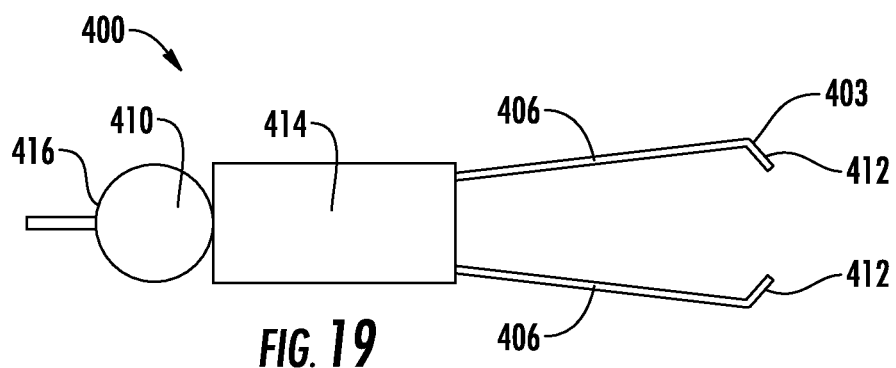
FIG. 19 shows a top view of a clip device, according to an embodiment of the present disclosure, in an open configuration.
Figure 20:
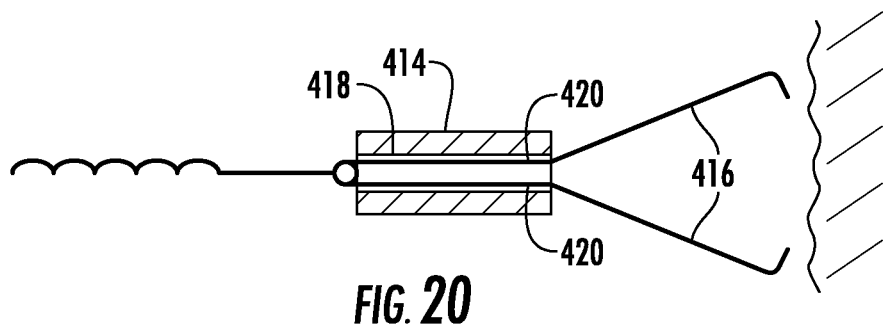
FIG. 20 shows a partial cross-sectional view of the clip device of FIG. 19 in the open configuration.
Figure 21:
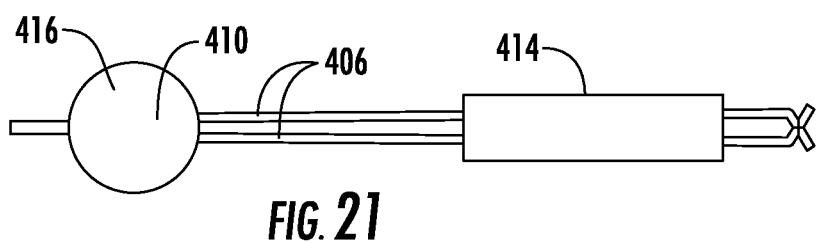
FIG. 21 shows a top view of the clip device of FIG. 19 in a closed configuration.

A clip device 400, according to another exemplary embodiment of the present disclosure is shown in FIGS. 19-21. In this embodiment, the clip device 400 includes clip arms 406, a slidable sheath 414 and a stop member 416. The clip arms 406, as with other embodiments, may be formed as wires. In this embodiment, the clip arms 406 extend between first ends 410 coupled to the stop member 416 and opposing second ends 412. Each of the clip arms 406, in this embodiment, is bent at a spring portion 420 radially outward away from a longitudinal axis of the clip device 400 biasing the clip arms 406 toward an open configuration, as shown in FIG. 20 (i.e., so that, when no external force is applied to the clip arms 406, the clip arms move outward to the open, e.g., tissue receiving, configuration). The sheath 414 is, in this embodiment, substantially cylindrical and includes a lumen 418 extending therethrough from a first end closest to the stop member 416 of the clip device 400 to a second end closest to the clipping end 403 of the clip device 400. The sheath 414 may be formed of any suitable material such as, for example, stainless steel or similar metals, polymers such as polycarbonate, Delrin or acrylonitrile butadiene styrene (ABS). The lumen 418 is sized and shaped to slidably receive the clip arms 406 therethrough. The stop member 416 is located at a side of the slidable sheath 414 closest to the stop member 416 and acts both as a stop for the slidable sheath 414 as well as a first grasping point for the gripper tool 10 as the sheath 414 is moved longitudinally along the clip arms 406. Thus, the sheath 414 is slidable along the clip arms 406 from the stop member 416 to the second ends 412 of the clip arms 406. The size of the clip arms 406 is configured so that when in their closed configuration, their combined width (i.e., dimension perpendicular to a longitudinal axis of the clip device 400) is larger than the inner diameter of the sheath 414. Additionally, the friction between the clip arms 406 and the sheath 414 will keep the sheath 414 from sliding longitudinally relative to the clip arms 406. Although the stop member 416 is shown to be substantially spherical in the figures, one skilled in the art would understand that the stop member 416 may have any shape so long as it is capable of being held by the grasping member.

In use, the clip device 400 is inserted into the body in an insertion configuration with the sheath 414 positioned adjacent the second ends 412 of the clip arms 406 so that the clip arms 406 are in a closed configuration. When the clip device 400 is positioned at the target site adjacent the tissue, the stop member 416 is held by a first gripper tool 10 while the sheath 414 is held by a second gripper tool 10. Holding the stop member 416 provides the leverage needed to move the sheath 414 toward the first ends 410 of the clip arms 406, allowing the clip arms 406 to spring to the biased open configuration depicted in FIG. 19. The second ends 412 of the clip arms 406 are then positioned on either side of the target tissue in the open configuration. With the second ends 412 in a desired position on the target tissue, the second gripper tool 10 is again used to move the sheath 414 toward the second ends 412 of the clip arms, moving the clip arms 406 toward one another to close the second ends 412 over the target tissue, as depicted in FIG. 21.

Figure 22:
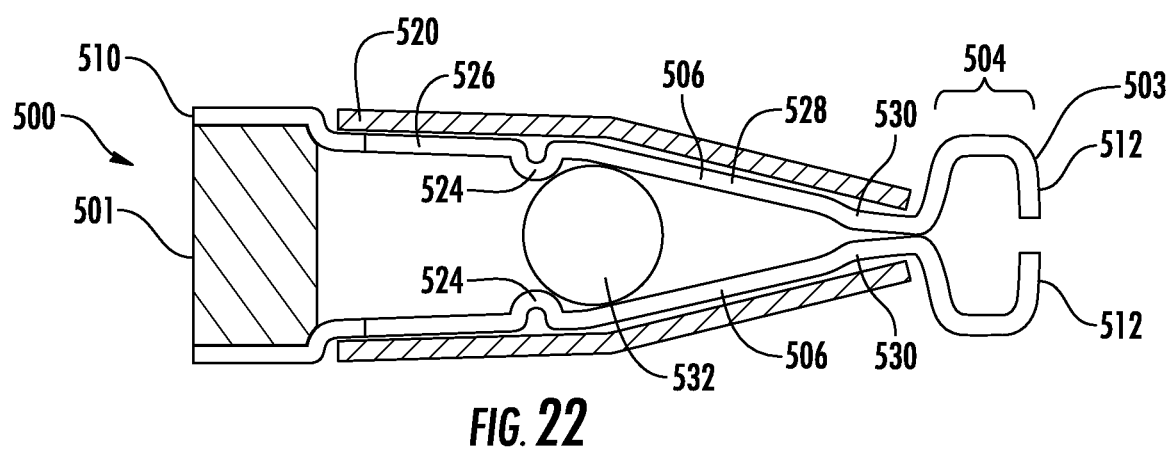
FIG. 22 shows a top view of a clip device, according to an exemplary embodiment of the present disclosure, in a closed configuration.
Figure 23:
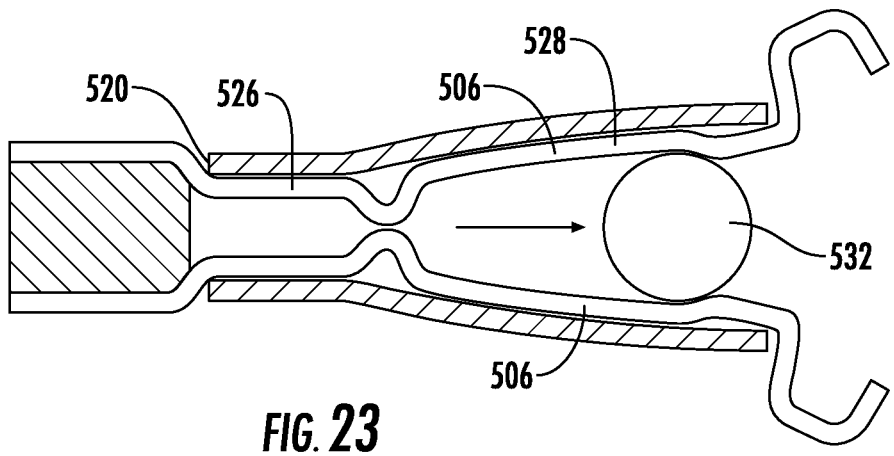
FIG. 23 shows a top view of the clip device of FIG. 22 in an open configuration.
Figure 24:
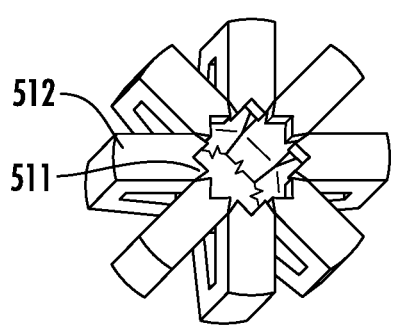
FIG. 24 shows a front view of clip arms of the clip device of FIG. 22 in the closed configuration.
Figure 25:
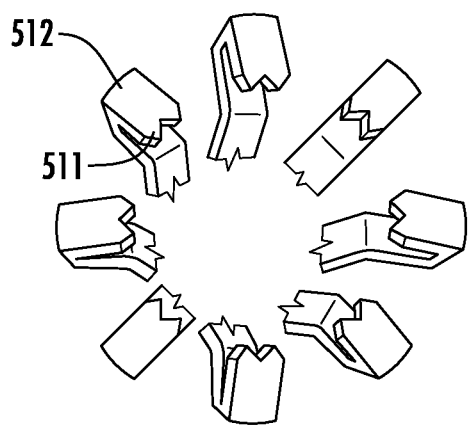
FIG. 25 shows a front view of clip arms of the clip device of FIG. 22 in the open configuration.

A clip device 500, according to another exemplary embodiment of the present disclosure, is shown in FIGS. 22-25. The clip device 500 uses a sliding ball actuator which acts as a fulcrum for a plurality of clip arms 506. In this embodiment, the clip arms 506 are positioned radially about a central longitudinal axis of the clip device 500, forming a substantially cylindrical clipping portion 504 of the clip device 500. The clip arms 506 are formed with teeth 511 at second ends 512 (i.e., ends closest to a clipping end 503 of the clip device 500) thereof, as shown in FIGS. 24-25. The teeth 511 enable the clip device 500 to capture tissue therein. Each of the clip arms 506 includes a grasping portion 526 extending from first ends 510 closest to the coupling end 501 of the clip device 500 to a first curved stop portion 524. The grasping portions 526 are configured to be pinched by the gripper tool 10 to actuate the clip arms 506. Each of the clip arms 506 also includes a pivoting portion 528 extending from the first curved stop portion 524 to a second curved stop portion 530. The pivoting portions 528 are configured to move about the sliding ball actuator 532 held therein. The grasping portions 526 and the pivoting portions 528 are separated by the first curved stop portion 524 of each clip arm 506. The first curved stop portions 524 and the second curved stop portions 530 prevent the sliding ball actuator 532 from moving out of the pivoting portion 528. The clip arms 506 are spring-biased toward the closed position via an overtube 520 positioned over an outer surface of the clip arms 506. That is, the elastomeric overtube 520 provides the force necessary to bias the clip arms 506 toward the closed position with the sliding ball actuator 532 at the first end of the pivoting portion 528 (i.e., at the first curved stop portion 524) closest to the coupling end 501. Although the teeth 511 and second ends 512 are described with respect to FIGS. 22-25, it will be understood that these features may be used in addition to or interchangeably with other embodiments in a substantially similar manner.

As noted above, when in the closed configuration, the sliding ball actuator 532 resides at a first end of the pivoting portion 528, as depicted in FIG. 22, with the elastomeric overtube 520 positioning the second ends 512 of the clip arms 506 toward one another into a closed, e.g., tissue gripping, configuration. When in use, the clip arms 506 are moved to the open, e.g., tissue receiving, configuration by pinching the grasping portion 526 of the clip arms 506 with the gripper tool 10. Because the elastomeric overtube 520 is, in this embodiment, cylindrical, and the plurality of clip arms are arranged in a cylindrical layout, the elastic overtube provides a surface that can be gripped at any angle. Thus, when the gripper tool 10 pinches the grasping portion 526, the sliding ball actuator 532 acts as a fulcrum about which the pivoting portion 528 moves, stretching the elastomeric overtube 520 to a larger diameter, as shown in FIG. 23. Continued pinching of the clip device 500 drives the sliding ball actuator 532 toward the second curved stop portions 530, further opening the clip arms 506 and further stretching the elastomeric overtube 520. When the second ends 512 of the clip arms 506 are positioned about target tissue as desired, the pinching force from the gripper tool 10 is released and the elastomeric overtube 520 forces the clip arms 506 closed, forcing the sliding ball actuator 532 toward the first curved stop portions 524. The closing of the elastomeric overtube 520 enables tissue captured within the teeth to be retained, allowing the tissue to be pulled in traction by the placement of a second clip device 500 attached to the opposite end of the tether traction clip device.

Figure 26:
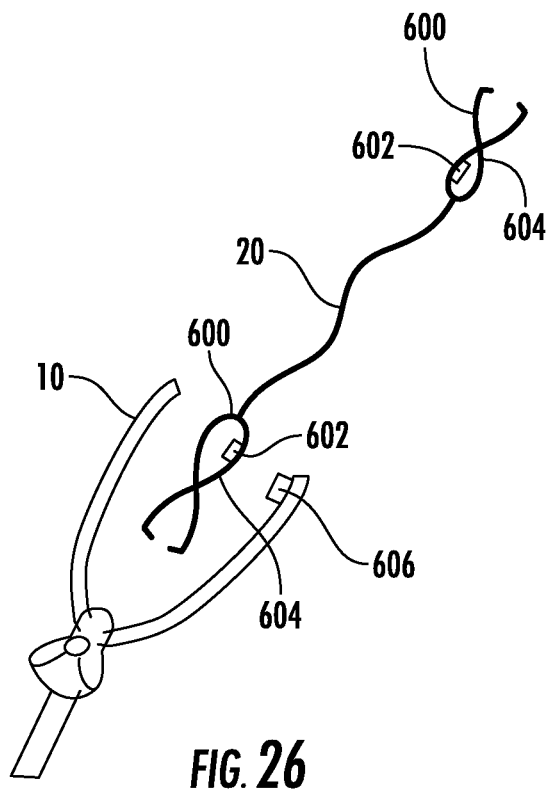
FIG. 26 shows a tether traction clip system according to an embodiment of the present disclosure.

When reaching and grasping for tools (i.e., the clip devices 100, 200, 300, 400, 500, and others described herein) at a distance in minimally invasive procedures, such as ESD and/or EMR procedures, one challenge may be contacting the grasping points on the clip devices with the gripper tool. In an exemplary embodiment, FIG. 26 depicts a tether traction clip system comprising magnets which may be used to provide simpler and faster interactions between the grasper and the grasping points on the clips, such as the clip devices 100, 200, 300, 400, 500, 1100, 1200, 1300, 1800, and others described herein. FIG. 26 depicts a gripper tool 10 and clip devices 600 coupled together via a tether 20. In this embodiment, each of the clip devices 600 include first magnets 602 of the same polarity positioned on grasping points 604 thereof. A second magnet 606 of reverse polarity is positioned on a grasping portion 608 of the gripper tool 10. Thus, when the gripper tool 10 is brought into the general vicinity of one of the clip devices 600, the magnets 602, 606 of the clip device 600 and the gripper tool 10, respectively, force the clip device 600 and the gripper tool 10 to self-orient to each other in a desired configuration. It is noted that the clip devices 600 of this embodiment are only exemplary and may take the form of any of clip devices 100, 200, 300, 400, 500, 1100, 1200, 1300, or 1800. For example, the first magnets 602 may be positioned on the proximal grasping portion 102 of the clip device 100, the proximal grasping portion 202 of the clip device 200, the first chamber of the clip device 300, the stop member 414 and/or sheath 416 of the clip device 400 or the grasping portion 526 of the clip device 500. In various embodiments, magnets may be embedded within and/or on the surface of conical gripping elements, a first member, and/or a second member.

Figure 27:
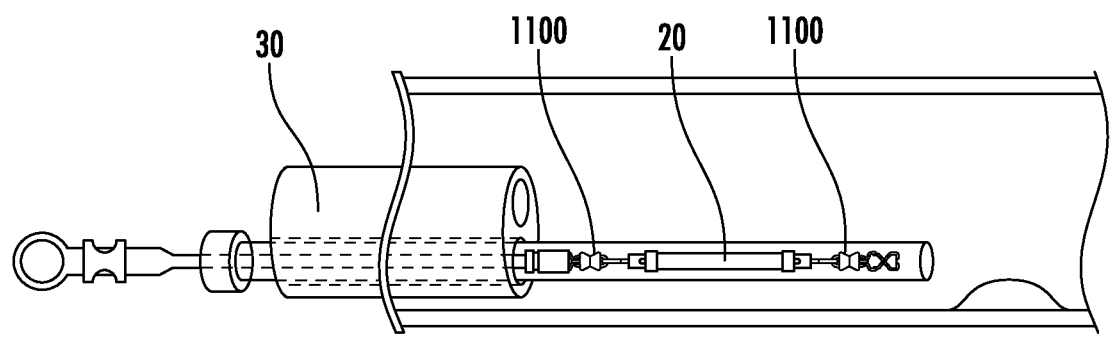
FIG. 27 shows a step of an exemplary method of use with the clip device of FIGS. 11A-11D.
Figure 28:
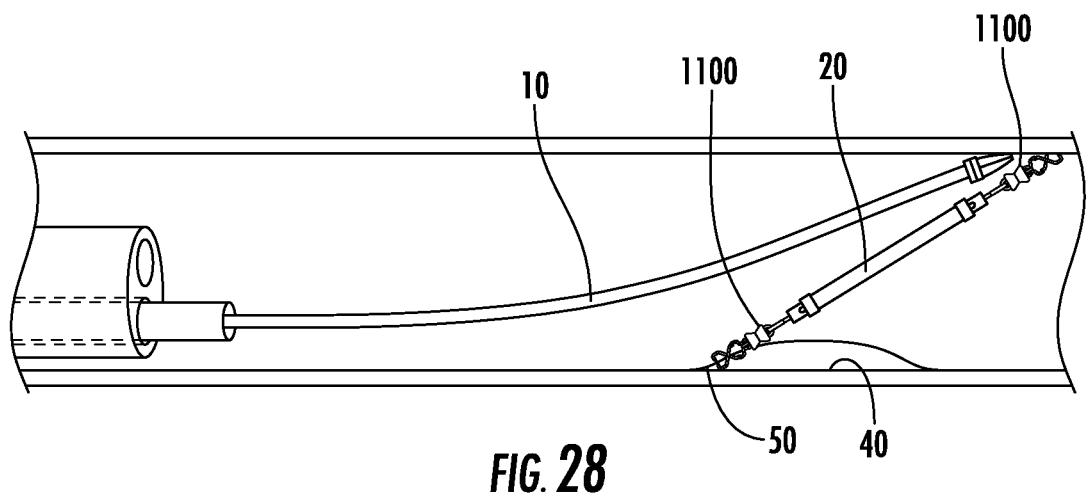
FIG. 28 shows a step of an exemplary method of use with the clip device of FIGS. 11A-11D.
Figure 29:
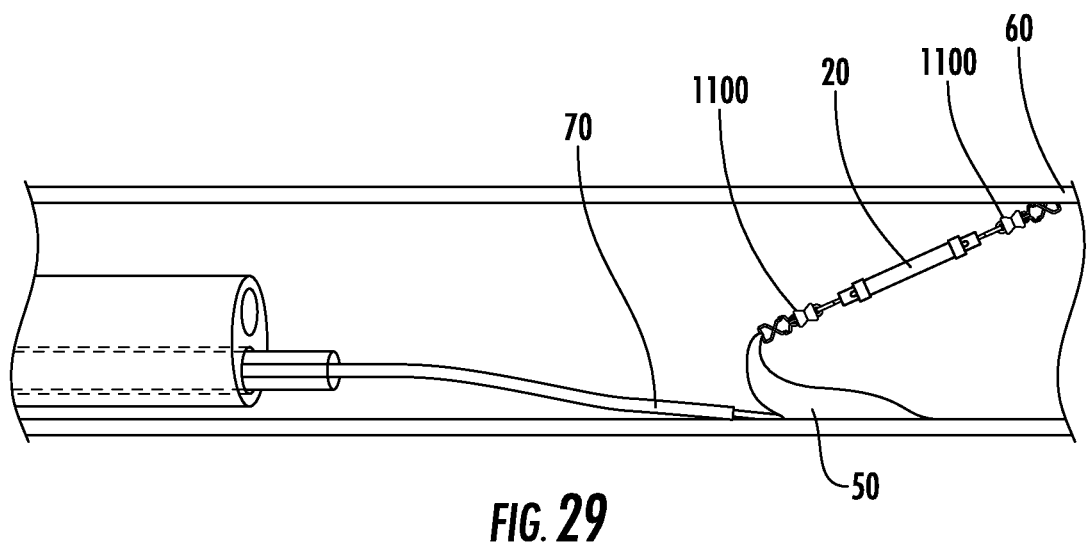
FIG. 29 shows a step of an exemplary method of use with the clip device of FIGS. 11A-11D.

An exemplary method for use of embodiments of clip devices for endoscopic submucosal dissection in accordance with present disclosure is illustrated in FIGS. 27-29. For simplification, FIGS. 27-29 depict clip device 1100 of FIGS. 11A-11D. However, it will be understood that any of the embodiments of clip devices described herein or otherwise within the scope of the present disclosure may be used in a substantially similar manner. Prior to insertion into the body, two clip devices 1100 are coupled to either end of an elongated elastomeric tether 20 to form the tether traction clip system 150. The clip devices 1100 and tether 20 are then inserted through a working channel of an endoscope 30 (or any other insertion device) using any known delivery device and inserted into the body (e.g., via a natural body lumen) to a site adjacent to a target portion of tissue, or a lesion, 40 to be resected. The clip devices 1100 and tether 20 are extended, or pushed, out of the endoscope working channel via the gripper tool 10, which is also positioned within the working channel proximal of the clip devices 100. When extended out of the working channel, the clip devices 1100 and tether 20 will lean against the adjacent tissue within the target body lumen. As would be understood by those skilled in the art, the lesion 40 (i.e., the target tissue) may have previously been marked and manipulated to make it more accessible (e.g., the tissue may have been pulled or pushed to alter folding of the tissue so that the lesion is exposed and not located deep within a fold of tissue). The target tissue may also have been injected with a bulking agent to lift the lesion 40 away from the underlying muscle layer.

The gripper tool 10 is then used to grasp the clipping device, e.g., members 1102, 1104 of the clip device 1100, opening the clip device 1100. It is noted that a longitudinal length of the jaws of the gripper tool 10 may preferably be selected to be smaller than a diameter of members 1102, 1104 of the clip devices 1100 such that the gripper tool 10 does not inadvertently grasp the tissue against which the clip devices 1100 may be adjacent (e.g., leaning against). The first clip device 1100, in the open configuration, is then positioned so that a first target portion of the lesion 40 (or adjacent tissue) is located between the separated arms of the grasper 1130. The gripper tool 10 then releases the one or more members 1102, 1104 of the first clip device 1100, permitting the spring 1128 attached to the members 1102, 1104 to draw toward one another under the natural bias of the device 1100 and also permitting the cam member 1118 to move into the spring space 1114 between the arms 1110 to close the device 1100, so that the first target portion of tissue is gripped and clipped by the closing arms of the grasper 1130. When a clip device 1100 has been clipped to the first target portion of tissue, another clip device 1100 is then attached to a nearby second target portion of tissue 60. The tether 20 applies tension between the two clip devices 1100 and, consequently, applies tension to the first and second target portions of tissue 60—in this example, the lesion 40 and the second target portion of tissue 60. With the two clip devices 100 in place, the gripper tool 10 is removed from the endoscope 30 and a resection device 70 is inserted through the working channel of the endoscope 30. The user then operates the resection device 70 in a known manner to make an initial incision in the lesion 40 permitting a resect a portion of the lesion (lesion flap 50) to lift away from underlying muscle via the tension created applied by the clip devices 1100 and tether 20. This enables the physician to more clearly observe the resection, e.g., cutting plane of the lesion, as shown in FIG. 29. As a greater surface area of the lesion is resected, the tension provided by the clip devices 1100 and tether 20 may decrease. At this point, the resection device 70 may be removed from the working channel and the gripper tool 10 may be reinserted. The gripper tool 10 is then used to reposition the clip device 1100 that was first placed into engagement with the tissue 60 on a different portion of tissue 60, so that a desired level of tension is again provided to the lesion flap 50 and the process for resecting the desired tissue free from surrounding tissue is repeated. This is repeated until the entirety of the lesion 40 has been resected from the underlying tissue. At this point, the additional device 1100 is detached from the tissue 60 via the gripper tool 10 and the tether traction clip system 150 along with the lesion tissue gripped by the clipping device 1100 is removed from the patient's body.

In various embodiments, the arms of a device may be multiple shapes. Such shapes may include one or more bends, jogs, or curves. The arms may be continuous and/or extensions of each other. The arms may include recesses, ridges, frictional surfaces, or additional materials configured to engage a tissue or a grasper. A device may have any number of arms, e.g., 1, 2, 3, 4, 6, 10, 20, etc. that may be made up of one or more wires. One or more graspers may be integral to, removably engaged, or attached to the ends of the arms.

In various embodiments, a channel of a device may be multiple shapes. The channel may substantially match the shape or curve of an arm or the channel may be shaped to accept one or more arms with a volume of unoccupied space about at least portions of the arm. Various channels throughout this disclosure are tapered, but a channel may have a substantially uniform diameter throughout and still be able to manipulate one or more arms.

In various embodiments, the shape of the first and second members may vary. For example, the members may include one or more angles configured to be engaged by a tool such that one or more of the members is displaced to engage the one or more arms. The members may be symmetrical or asymmetrical with respect to each other. For example, the members may be substantially frustum-shaped such that an apex of each frustum is oriented toward the other member, so as to form an hourglass shape when they are in substantial contact with each other. The members may be configured such that the proximal and/or distal member is displaced while the other member is fixed or is also displaced.

In various embodiments, one or more arms of a device may be used to manipulate a grasper. The arms may open and close to receive or engage the grasper. The motion of a second end of the arms may create opposing movement at a second end of the jaws of the grasper (e.g., as illustrated in FIG. 11B). The arms of a device may be arranged to be closed in order to open the jaws of a grasper and vice versa.

In various embodiments, other methods of using a device described herein may include inserting a tissue clipping device into a patient. A member of the clipping device may be engaged by another medical device from a plurality of angles relative to a longitudinal axis of the clipping device. The member of the clipping device may be displaced apart from the other member such that it engages and manipulates one or more arms of the device into an open configuration. The device may be manipulated such that the arms receive a tissue. The member may be displaced into substantial contact with the other member such that it disengages from the one or more arms and the arms transition from the open configuration to a closed configuration. The device may be fixed to a tissue. The device may be moved while the device is engaged with a tissue such that the device and the tissue move together for removal from a patient (e.g., resection).

In various embodiments, the arms of a device may comprise a single wire or may be multiple separate wires. The one or more wires may be attached to a member and may extend through another member. The spring portion(s) of the one or more wires may bias the arms toward or away from each other.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims. All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A tissue clipping device, comprising:
   a first member;
   a second member slidably disposed with respect to the first member;
   a plurality of arms, each of the plurality of arms extending from a first end to a second end, the first end of each of the plurality of arms being received within at least one of the first member or the second member; and
   wherein the first member and the second member have cooperating surfaces adjacent to each other and extending circumferentially therearound and configured to displace the first member and second member relative to each other along the longitudinal axis of the clipping device in response to an application of a radially-inwardly directed force to both of the adjacent cooperating surfaces to cause the plurality of arms to move between an open configuration and a closed configuration.

2. The tissue clipping device of claim 1, wherein each of the plurality of arms includes a spring portion configured to form a spring space between the spring portions of each of the plurality of arms.

3. The tissue clipping device of claim 2, further comprising a cam member extending from a first end to a second end, the first end of the cam member being fixedly coupled to the second member, and the second end of the cam member being configured to engage the spring space.

4. The tissue clipping device of claim 3, wherein when the first and second members are displaced apart from each other the second end of the cam member moves into of engagement with the spring space and the plurality of arms assume the open configuration, and when the first and second members are displaced toward each other the second end of the cam member moves out of engagement with the spring space and the plurality of arms transition to the closed configuration.

5. The device of claim 1, wherein the cooperating surfaces of the first member and the second member include angled-surfaces configured to displace the first member and the second member to be spaced apart from each other longitudinally in response to application of the radially-inwardly directed force to the angled-surfaces.

6. The tissue clipping device of claim 1, further comprising a grasper having a first end engaged between the plurality of arms and a second end comprising jaws configured to engage tissue.

7. The tissue clipping device of claim 6, wherein the grasper comprises first and second grasper arms in a crossing configuration in which the second ends of the grasper arms move away from each other when the first ends of the grasper arms move closer together.

8. The tissue clipping device of claim 1, wherein the plurality of arms are biased to the closed configuration.

9. The tissue clipping device of claim 1, wherein the plurality of arms are received within the second member.

10. The tissue clipping device of claim 1, further comprising a cam movable with the second member to cause the plurality of arms to move from the closed configuration to the open configuration.

11. The tissue clipping device of claim 1, wherein the plurality of arms are mechanically constrained with respect to the first member such that as the first member is longitudinally displaced with respect to the second member, the plurality of arms are displaced.

12. The tissue clipping device of claim 1, wherein the second member is disposed about the plurality of arms and is positioned between the plurality of arms and the first member, and the first member is slidable with respect to the second member and the plurality of arms to cause the plurality of arms to move between the open configuration and the closed configuration.

13. The tissue clipping device of claim 1, wherein the cooperating surfaces include surfaces inclined towards each other and configured to displace the first and second members apart from each other longitudinally in response to application of radially-inwardly directed to force to the inclined surfaces.

14. A tissue clipping device, comprising:
a grasping portion comprising a first member and a second member longitudinally slidable with respect to each other along the longitudinal axis of the tissue clipping device; and
a plurality of arms, each of the plurality of arms extending from a first end to a second end, the first end of each of the plurality of arms being received within at least one of the first member or the second member;
wherein adjacent ends of the first member and the second member are configured to be displaced to be spaced apart relative to each other along the longitudinal axis of the tissue clipping device in response to application of a radially-inwardly directed force to cooperating surfaces of the first member and the second member to transition the plurality of arms between a closed configuration and an open configuration.

15. The tissue clipping device of claim 14, wherein the plurality of arms have opposed surfaces sloped with respect to the longitudinal axis of the tissue clipping device, such that when the first and second members are displaced apart from each other, the sloped opposed surfaces of the plurality of arms move into engagement with a channel in at least one of the first member or the second member, and when the first and second members are displaced toward each other, the sloped opposed surfaces of the plurality of arms are moved out of engagement with the channel.

16. The tissue clipping device of claim 14, wherein the plurality of arms are biased to the closed configuration.

17. The tissue clipping device of claim 14, wherein the first and second members include adjacent angled surfaces configured to displace the first and second members apart from each other in response to application of the radially-inwardly directed force to the angled surfaces.

18. The tissue clipping device of claim 14, wherein the plurality of arms are formed of a single body bent at a medial portion, the medial portion forming the first ends of the plurality of arms.

19. The tissue clipping device of claim 14, further comprising a grasper disposed between the second ends of the plurality of arms.

20. A tissue clipping device, comprising:
a grasping portion comprising a first member and a second member longitudinally slidable with respect to each other along the longitudinal axis of the tissue clipping device; and
a plurality of arms, each of the plurality of arms extending from a first end to a second end, the first end of each of the plurality of arms being received within at least one of the first member or the second member;
wherein the first member and the second member are configured to be displaced relative to each other along the longitudinal axis of the tissue clipping device in response to application of a radially-inwardly directed force to cooperating surfaces at ends of the first member and the second member to transition the plurality of arms between a closed configuration and an open configuration.

* * * * *